(12) United States Patent
Sirota et al.

(10) Patent No.: US 9,044,504 B1
(45) Date of Patent: Jun. 2, 2015

(54) USING CONFIGURED APPLICATION PRICING TO DETERMINE END USER FEES FOR USE OF INVOCABLE SERVICES

(75) Inventors: Peter Sirota, Seattle, WA (US); Don Johnson, Seattle, WA (US); Gaurav D. Ghare, Seattle, WA (US); Tushar Jain, Bellevue, WA (US); Alan S. Geller, Redmond, WA (US)

(73) Assignee: Amazon Technologies, Inc., Reno, NV (US)

( * ) Notice: Subject to any disclaimer, the term of this patent is extended or adjusted under 35 U.S.C. 154(b) by 413 days.

(21) Appl. No.: 13/071,368

(22) Filed: Mar. 24, 2011

Related U.S. Application Data

(62) Division of application No. 11/618,480, filed on Dec. 29, 2006, now Pat. No. 7,925,554.

(51) Int. Cl.
| | |
|---|---|
| G06Q 30/00 | (2012.01) |
| G07F 19/00 | (2006.01) |
| G06F 7/00 | (2006.01) |
| A61K 48/00 | (2006.01) |

(52) U.S. Cl.
CPC ..................... *A61K 48/00* (2013.01)

(58) Field of Classification Search
USPC .......................................................... 705/34
See application file for complete search history.

(56) References Cited

U.S. PATENT DOCUMENTS

| | | | | |
|---|---|---|---|---|
| 5,826,244 | A | | 10/1998 | Huberman ....................... 705/37 |
| 5,958,016 | A | | 9/1999 | Chang et al. .................. 709/229 |
| 6,014,651 | A | * | 1/2000 | Crawford ....................... 705/400 |
| 6,078,906 | A | | 6/2000 | Huberman ....................... 705/37 |
| 6,086,618 | A | * | 7/2000 | Al-Hilali et al. .................. 703/2 |
| 6,175,869 | B1 | | 1/2001 | Ahuja et al. ................... 709/226 |
| 6,470,386 | B1 | * | 10/2002 | Combar et al. ............... 709/224 |

(Continued)

FOREIGN PATENT DOCUMENTS

| | | | |
|---|---|---|---|
| EP | 1920393 A2 | * | 5/2008 |
| WO | 2007/052285 A2 | | 5/2007 |

OTHER PUBLICATIONS

Currie W, Seltsikas P. Delivering Business Critical Information Systems Though Application Service Providers: The Need for a Market Segmentation Strategy. International Journal of Innovation Management [serial online]. Sep. 2001;5(3):323. Available from: Business Source Complete, Ipswich, MA.*

(Continued)

*Primary Examiner* — Ashford S Hayles
(74) *Attorney, Agent, or Firm* — Seed IP Law Group PLLC

(57) ABSTRACT

Techniques are described for facilitating use of invocable services by applications in a configurable manner. In at least some situations, the invocable services are Web services or other network-accessible services that are made available by providers of the services for use by others in exchange for fees defined by the service providers. The described techniques facilitate use of such invocable services by applications in a manner configured by the application providers and the service providers, including to track use of third-party invocable services by applications on behalf of end users and to allocate fees that are charged end users between the applications and the services as configured by the providers of the applications and services. In some situations, the configured pricing terms for a service specify fees for end users that differ in one or more ways from the defined fees charged by the provider of that service.

30 Claims, 15 Drawing Sheets

(56) References Cited

U.S. PATENT DOCUMENTS

| | | | |
|---|---|---|---|
| 6,567,850 B1* | 5/2003 | Freishtat et al. | 709/224 |
| 6,594,692 B1* | 7/2003 | Reisman | 709/219 |
| 6,728,266 B1* | 4/2004 | Sabry et al. | 370/468 |
| 6,748,502 B2 | 6/2004 | Watanabe et al. | 711/158 |
| 6,816,882 B1* | 11/2004 | Conner et al. | 709/203 |
| 6,938,007 B1* | 8/2005 | Iulianello et al. | 705/34 |
| 7,020,628 B2* | 3/2006 | Peterson et al. | 705/32 |
| 7,080,051 B1 | 7/2006 | Crawford | 705/400 |
| 7,334,225 B2 | 2/2008 | Boonie et al. | 717/171 |
| 7,356,512 B2 | 4/2008 | Okita et al. | 705/51 |
| 7,370,075 B2 | 5/2008 | Farquharson et al. | 709/203 |
| 7,376,729 B2* | 5/2008 | Tanaka et al. | 709/224 |
| 7,386,483 B1* | 6/2008 | Lee et al. | 705/26.3 |
| 7,418,426 B1* | 8/2008 | Reunert et al. | 705/40 |
| 7,447,642 B2 | 11/2008 | Bodin | 705/1 |
| 7,506,021 B2 | 3/2009 | Polan et al. | 709/201 |
| 7,549,153 B2 | 6/2009 | Butterworth et al. | 719/317 |
| 7,613,817 B2* | 11/2009 | Eibach et al. | 709/231 |
| 7,660,887 B2 | 2/2010 | Reedy et al. | 709/224 |
| 7,689,430 B2 | 3/2010 | Freemantle et al. | 705/1 |
| 7,711,832 B1 | 5/2010 | Champion et al. | 709/228 |
| 7,729,955 B2 | 6/2010 | Frederick et al. | 705/26 |
| 7,734,515 B1* | 6/2010 | Frederick et al. | 705/26.1 |
| 7,827,104 B2* | 11/2010 | Posabella et al. | 705/40 |
| 7,991,764 B2* | 8/2011 | Rathod | 707/713 |
| 2001/0037415 A1* | 11/2001 | Freishtat et al. | 709/328 |
| 2001/0051929 A1 | 12/2001 | Suzuki | 705/52 |
| 2002/0048369 A1 | 4/2002 | Ginter et al. | 380/277 |
| 2002/0083003 A1* | 6/2002 | Halliday et al. | 705/52 |
| 2002/0116278 A1* | 8/2002 | Meyer et al. | 705/26 |
| 2002/0120461 A1 | 8/2002 | Kirkconnell-Ewing et al. | 705/1 |
| 2002/0120519 A1 | 8/2002 | Martin et al. | 705/21 |
| 2002/0143819 A1* | 10/2002 | Han et al. | 707/513 |
| 2002/0152143 A1* | 10/2002 | Sanada et al. | 705/32 |
| 2002/0161676 A1 | 10/2002 | Vadlamani | 705/30 |
| 2002/0164025 A1* | 11/2002 | Raiz et al. | 380/231 |
| 2003/0061067 A1* | 3/2003 | Atwal et al. | 705/1 |
| 2003/0061404 A1 | 3/2003 | Atwal et al. | 709/328 |
| 2003/0079047 A1* | 4/2003 | Fitts et al. | 709/310 |
| 2003/0110242 A1 | 6/2003 | Brown et al. | 709/222 |
| 2003/0187800 A1 | 10/2003 | Moore et al. | 705/52 |
| 2003/0195813 A1 | 10/2003 | Pallister et al. | 705/26 |
| 2004/0015448 A1 | 1/2004 | Asano | 705/52 |
| 2004/0064411 A1* | 4/2004 | Tsui et al. | 705/40 |
| 2004/0073661 A1 | 4/2004 | Eibach et al. | 709/224 |
| 2004/0117311 A1* | 6/2004 | Agarwal et al. | 705/52 |
| 2004/0122926 A1 | 6/2004 | Moore et al. | 709/223 |
| 2004/0176988 A1* | 9/2004 | Boughannam | 705/4 |
| 2004/0220878 A1* | 11/2004 | Lao et al. | 705/51 |
| 2004/0243583 A1 | 12/2004 | Olsen | 707/10 |
| 2004/0249927 A1* | 12/2004 | Pezutti | 709/223 |
| 2004/0267645 A1* | 12/2004 | Pollari | 705/34 |
| 2005/0044197 A1* | 2/2005 | Lai | 709/223 |
| 2005/0065879 A1* | 3/2005 | Birch et al. | 705/40 |
| 2005/0125389 A1 | 6/2005 | Hazzard et al. | 707/3 |
| 2005/0131773 A1 | 6/2005 | Daur et al. | 705/26 |
| 2005/0165655 A1* | 7/2005 | Kobrosly et al. | 705/26 |
| 2005/0165656 A1* | 7/2005 | Frederick et al. | 705/26 |
| 2006/0004771 A1* | 1/2006 | Enenkiel | 707/10 |
| 2006/0010236 A1* | 1/2006 | Meiser et al. | 709/226 |
| 2006/0015463 A1 | 1/2006 | Gupta et al. | 705/52 |
| 2006/0036553 A1* | 2/2006 | Gupta et al. | 705/52 |
| 2006/0041641 A1 | 2/2006 | Breiter et al. | 709/219 |
| 2006/0059057 A1* | 3/2006 | Peterson et al. | 705/32 |
| 2006/0080257 A1 | 4/2006 | Vaughan et al. | 705/51 |
| 2006/0265490 A1* | 11/2006 | Pishevar et al. | 709/223 |
| 2007/0100886 A1 | 5/2007 | Steeb et al. | 707/104.1 |
| 2007/0208851 A1 | 9/2007 | Unkenholz et al. | 709/224 |
| 2007/0265982 A1* | 11/2007 | Kalervo et al. | 705/59 |
| 2007/0288933 A1* | 12/2007 | Shariff et al. | 719/318 |
| 2007/0289028 A1 | 12/2007 | Vaughan et al. | 726/30 |
| 2008/0040510 A1 | 2/2008 | Warner et al. | 709/246 |
| 2008/0086490 A1 | 4/2008 | Paliwal et al. | 707/101 |
| 2008/0086564 A1 | 4/2008 | Putman et al. | 709/227 |
| 2008/0091818 A1* | 4/2008 | Bailey et al. | 709/224 |
| 2008/0109363 A1 | 5/2008 | Fassett | 705/52 |
| 2008/0154796 A1 | 6/2008 | Pallister et al. | 705/36 |
| 2008/0235119 A1 | 9/2008 | Agarwal et al. | 705/34 |
| 2008/0249904 A1 | 10/2008 | Eibach et al. | 705/34 |
| 2009/0099940 A1 | 4/2009 | Frederick et al. | 705/26 |
| 2009/0276771 A1 | 11/2009 | Nickolov et al. | 717/177 |
| 2009/0298462 A1* | 12/2009 | Karlsson et al. | 455/406 |
| 2009/0307135 A1* | 12/2009 | Gupta et al. | 705/44 |

OTHER PUBLICATIONS

McAllister N. Open Source Apps Get the Job Done. Infoworld [serial online]. Aug. 8, 2005;27(32):36-47. Available from: Computer Source, Ipswich, MA.*

Currie W, Seltsikas P. Delivering Business Critical Information Systems Though Application Service Providers: The Need for a Market Segmentation Strategy. International Journal of Innovation Management [serial online]. Sep. 2001 ;5(3):323. Available from: Business Source Complete, Ipswich, MA.*

"Metering and Accounting for Web Services," IBM®, Jul. 2001, retrieved from http://www-106.ibm.com/developerworks/library/ws-maws/, 6 pages.

"NTT Com to Launch Asia's First UDDI Registry on Oct. 9," Oct. 8, 2002, NTT Communications, retrieved Sep. 9, 2005, from http://www.ntt.com/release_e/news02/0010/1008.html, 3 pages.

"The Bowstreet™ Business Web Exchange Fuels B2B Revolution With First-of-its-Kind 'Web Services' Marketplace," Mar. 16, 2000, Bowstreet.com Inc., retrieved Sep. 9, 2005, from http://web.archive.org/web/20010219033902/http://www.bowstreet.com/news/press_release . . . , 4 pages.

"The Web Services Architect: Catalysts for Fee-Based Web Services," IBM®, Nov. 2001, retrieved from http://www-106.ibm.com/developerworks/library/ws-arc6/, 7 pages.

"Web Service Use Case," ContentGuard Holdings, Inc., retrieved Aug. 9, 2005, from http://www.contentguard.com/reference/docs/SimpleWebServiceExampleContent.htm, 4 pages.

"Web Service Use Case: Travel Reservation—Use Case May 5, 2002," W3C®, May 2002, retrieved Aug. 9, 2005, from http://www.w3.org/2002/06/ws-example, 9 pages.

"Web Services Architecture Usage Scenarios—W3C Working Draft Jul. 30, 2002," W3C®, Jul. 2002, retrieved Aug. 2, 2005, from http://www.w3.org/TR/2002/WD-ws-arch-scenarios-20020730/, 78 pages.

"Web Services Marketplace," retrieved Sep. 9, 2005, from http://web.archive.org/web/20010404230735/www/epicentric.com/solutions/mkt.jsp, 4 pages.

Actional™, The Web Services Management Platform: Managing the Impact of Change in an Enterprise Web Services Network—Mar. 2003, retrieved Nov. 7, 2003, from http://www.actional.com/downloads/products/managing.enterpriseweb.services.network.pdf , 26 pages.

Actional™, Web Services Management Platform, retrieved Nov. 7, 2003, from http://www.actional.com/products/web_services/index.asp, 3 pages.

Albrecht, C., et al., "Marketplace and Technology Standards for B2B Ecommerce: Progress and Challenges," MIS Quarterly Special Issue on Standard Making, International Conference on Information Systems, Dec. 2003, Seattle, WA, pp. 188-209, 22 pages.

Allidex, Frequently Asked Questions, retrieved Nov. 4, 2003, from http://www.allidex.com/faq.html, 4 pages.

Amazon.com, Inc., Associates: Enhance Your Site Using Web Services, retrieved Nov. 4, 2003, from http://www.amazon.com/gp/browse.html/ref=sc_bb_1_1/104-7530911-9659969?no=3435361&me=A3.6.L, 2 pages.

Amazon.com, Inc. Developers: Build Solutions for Amazon Partners, retrieved Nov. 4, 2003, from http://www.amazon.com/gp/browse.html/ref=sc_bb_1_1/104-7530911-9659969?no=3435361&me=A3.6.L, 2 pages.

Amazon.com, Inc., Sellers and Vendors: Sell More Using Web Services, retrieved Nov. 4, 2003, from http://www.amazon.com/gp/browse.html/ref=sc_bb_1_1/104-7530911-9659969?no=3435361&me=A3.6.L, 1 page.

(56) References Cited

OTHER PUBLICATIONS

Amazon.com, Inc., Web Services FAQ's, retrieved Nov. 4, 2003, from http://www.amazon.com/gp/browse.html/ref=sc_bb_1_0/104-7530911-9659969?no=3435361&me=A3.6.L, 11 pages.
Amazon.com, Inc., Web Services, retrieved Nov. 4, 2003, from http://www.amazon.com/gp/browse.html/104-7530911-9659969?node=3435361, 2 pages.
Andrews, T., et al., "Specification: Business Process Execution Language for Web Services Version 1.1," IBM developerWorks, May 5, 2003, retrieved Jan. 31, 2005, from http://www-106.ibm.com/developerworks/webservices/library/ws-bpel/, 124 pages.
Binstock, A., "Staking New Territory, Breaking New Ground," retrieved Sep. 9, 2005, from http://archive.devx.com/javaSR/articles/binstock/binstock.asp, 6 pages.
Box, Don et al., "Web Services Policy Framework (WS-Policy)," Jun. 2, 2003, retrieved Sep. 12, 2005, from ftp://www6.software.ibm.com/software/developer/library/ws-policy2003.pdf, 21 pages.
Brown, R., "Epicentric Unveils Web Services E-Hub," Mar. 21, 2001, Line56.com, retrieved Sep. 9, 2005, from http://www.line56.com/print/default.asp?ArticleID=2287, 2 pages.
Bunting, Doug et al., "Web Services Composite Application Framework (WS-CAF)," Jul. 28, 2003, retrieved Sep. 12, 2005, from http://www.oasis-open.org/committees/download.php/4343/WS-CAF%20Primer.pdf, 23 pages.
Burbeck, S., "The Tao of E-Business Services—The Evolution of Web Applications Into Service-Oriented Components With Web Services," Oct. 2000, IBM®, http://www-4.ibm.com/software/developer/library/ws-tao/index.html, 13 pages.
Business Wire, "Desktop.com Introduces Devtop, the First Integrated Platform for Building, Deploying, and Distributing Web-Based Applications," Jun. 26, 2000, retrieved Sep. 8, 2005, from http://www.findarticles.com/p/articles/mi_m0EIN/is_2000_June_26/ai_62915951/print, 2 pages.
Clark, M., "Business Architecture for a Web Services Brokerage—Understanding the Business Context of Web Services," Aug. 1, 2001, retrieved Aug. 2, 2005, from http://www.webservicesarchitect.com/content/artciles/clark01print.asp, 5 pages.
CPA2Biz, Inc., "New Rivio Business Services Suite," Apr. 18, 2001, retrieved Sep. 8, 2005, from https://www.cpa2biz.com/Corp/Press+Releases/PR_WebTools_18APR01.htm, 3 pages.
CPA2Biz, Inc., "Verizon Unveils Rivio Web Services Suite for Small Business Customers," May 29, 2001, retrieved Sep. 22, 2005, from https://www.cpa2biz.com/Corp/Press+Releases/PR_VERIZON_29MAY01.htm, 3 pages.
E2OPEN™, E2open Products, retrieved Nov. 7, 2003, from http://www.e2open.com/products/, 3 pages.
E2OPEN™, The E2open Integration Platform, retrieved Nov. 7, 2003, from http://www.e2open.com/downloads/e2open_integration_platform_datasheet.pdf, 5 pages.
ebizQ, Product Quicktake, retrieved Nov. 7, 2003, from http://www.ebizq.net/reports/1884.html?download=1, 2 pages.
Grand Central™ Communications website, retrieved Nov. 6, 2003, from http://www.grandcentral.com/products/, 2 pages.
Grand Central™ Communications, Frequently Asked Questions, retrieved Nov. 6, 2003, from http://www.grandcentral.com/products/faqs/index_html, 5 pages.
Irani, R., "Web Services Intermediaries—Adding Value to Web Services," Nov. 21, 2001, retrieved Aug. 2, 2005, from http://www.webservicesarchitect.com/content/articles/irani07print.asp, 5 pages.
Jamcracker, Inc., "Jamcracker announces Pivot Path: Fully integrated software suite for Identity Management," Nov. 11, 2003, retrieved Sep. 12, 2005, from http://web.archive.org/web/20040607054618/http://jamcracker.com/pivot_path_release.pdf, 2 pages.
Khare, R., "Whiz-Bangery, Indeed: Primordial's WSBANG," Nov. 16, 2001, retrieved Sep. 9, 2005, from http://lair.xent.com/pipermail/fork/2001-Nov./006569.html, 2 pages.
Lee, Yvonne L., "Strikelron's Hot for Web Services," *SD Times*, Jun. 1, 2004, retrieved Sep. 12, 2005, from http://www.strikeiron.com/doc/SDTimes060104.pdf, 1 page.

Levitt, J., "From EDI to XML and UDDI: A Brief History of Web Services," Oct. 1, 2001, InformationWeek, retrieved Sep. 9, 2005, from http://www.informationweek.com/story/IWK20010928S0006, 3 pages.
Leymann, F., "Web Services Flow Language (WSFL 1.0)," IBM Software Group, May 2001, 108 pages.
Oasis, UDDI.org, retrieved Sep. 8, 2005, from http://www.uddi.org/find.html, 2 pages.
PayPal.com, Recurring Billing Service: How it Works, retrieved Dec. 5, 2006, from http://www.paypal.com/cgi-bin/webscr?cmd=_payflow-recurring-billing-integration-outside, 2 pages.
PayPal.com, Recurring Billing Service: FAQs, retrieved Dec. 5, 2006, from http://www.paypal.com/cgi-bin/webscr?cmd=_payflow-recurring-billing-faq-outside, 3 pages.
Radding, A., "Generating Revenue from Web Services—Six Vendors With the Right Tools," Jan. 20, 2003, retrieved from http://72.14.207.104/search?q=cache:W5EXBA4Lr54J:home. comcast.net/~alan-radding/iaws.pdf+generating+revenue+from+web+services+radding&hl=en&gl=us&ct=clnk&cd=3, 4 pages.
Sabre Travel Network, Sabre Travel Network Launches Web Services Capabilities for Agents, Jul. 28, 2003, retrieved Sep. 13, 2005, from http://phx.corporate-ir.net/phoenix.zhtml?c=73098&p=IROL-NewsText&t=Regular&id=435603&logo=logo03, 2 pages.
SalCentral, Subscription of Web Services, Oct. 5, 2003, retrieved Sep. 7, 2005, from http://web.archive.org/web/20031005075820/www.salcentral.com/salnet/wpsubws.htm, 5 pages.
SalCentral, The Napster of Web Services, Oct. 4, 2003, retrieved Sep. 7, 2005, from http://web.archive.org/web/20031004143406/www.salcentral.com/salnet/webservicesnapster.asp, 2 pages.
SalCentral, WSDL, SOAP and Web Services and Quality Assurance and promotion, Oct. 4, 2003, retrieved Sep. 7, 2005, from http://web.archive.org/web/20031004143940/www.salcentral.com/salnet/webservicewhat.as.p, 2 pages.
SalCentral, WSDL, SOAP, Web Services Search Engine and Web Service Tracking, Oct. 11, 2003, retrieved Oct. 6, 2005, from http://web.archive.org/web/20031011101544/www.salcentral.com/salnet/webserviceswsdln.e.asp, 1 page.
Samtani, G., et al., "Integration Brokers and Web Services—Will Web Services Support Be Just Another Feature?" Jan. 30, 2002, retrieved Aug. 2, 2005, from http://www.webservicesarchitect.com/content/articles/samtani03print.asp, 5 pages.
Schofield, J., "The Third Era Starts Here," *The Guardian*, May 29, 2003, retrieved Nov. 4, 2003, from http://www.guardian.co.uk/print/0,3858,4678440-110837,00.html, 3 pages.
Siddiqui, B., "UDDI Based Electronic Marketplaces—Easier Integration With UDDI and WSDL," Feb. 20, 2002, retrieved Aug. 2, 2005, from http://www.webservicesarchitect.com/content/articles/siddiqui02print.asp, 4 pages.
Sirin, E., et al., "Semi-automatic Composition of Web Services Using Semantic Descriptions," In *Web Services: Modeling, Architecture and Infrastructure workshop in ICEIS 2003*, Angers, France, Apr. 2003, from http://www.mindswap.org/papers/composition.pdf, 9 pages.
Smith, Rick, "Striking While the Iron is Red Hot: StrikeIron Unveils Its Web Network," *LocalTechWire*, Jun. 25, 2004, retrieved Sep. 22, 2005, from http://www.localtechwire.com/article.cfm?u=8509, 3 pages.
SoftwareMarkets.com, Frequently Asked Questions from Developers, Sep. 18, 2000, retrieved Sep. 8, 2005, from http://web.archive.org/web/20000918003355/www.softwaremarkets.com/info/faqdevs.html, 3 pages.
Sterling Commerce, Sterling Information Broker, retrieved Nov. 10, 2003, from http://www.sterlingcommerce.com/PDF/Solutions/Sterling/SC0040.InfoBrokerOver.6-02.pdf, 4 pages.
Sterling Commerce, Sterling Information Broker, retrieved Nov. 10, 2003, from http://www.sterlingcommerce.com/solutions/em/commerce/iibs.html, 3 pages.
StrikeIron, Inc., "StrikeIron Launches the Web Services Business Network," Jun. 23, 2004, retrieved Sep. 8, 2005, from http://www.strikeiron.com/news/si_launches.aspx, 3 pages.

(56) References Cited

OTHER PUBLICATIONS

StrikeIron, Inc., "StrikeIron Web Services Business Network Overview," retrieved Sep. 12, 2005, from http://www.strikeiron.com/doc/StrikeIronWebServicesBusinessNetworkOverview.pdf, 24 pages.

StrikeIron, Inc., Frequently Asked Questions, retrieved Dec. 5, 2006, from http://www.strikeiron.com/info/faqs_p.aspx, 5 pages.

StrikeIron, Inc., What is Invoke Through Compensation, retrieved Dec. 5, 2006, from http://www.strikeiron.com/info/whatisinvokethrough.aspx, 3 pages.

Taft, Darryl K., "Start-Up Presents ASP Opportunity for Java Developers," CRN, Jul. 31, 2000, retrieved Sep. 20, 2005, from http://www.crn.com/sections/breakingnews/breakingnews.jhtml?articleId=18834381, 3 pages.

Tolksdorf, R., et al., "A Web Service Market Model Based on Dependencies," retrieved Sep. 9, 2005, from http://www.wiwiss.fu-berlin.de/suhl/bizer/pub/p49-tolksdorf.html, 4 pages.

UNISYS, Web Service Marketplace, retrieved Nov. 4, 2003, from http://www.unisysfsp.com/default.aspx?catID+16, 2 pages.

W3C, "WS Choreography Model Overview," Mar. 24, 2004, retrieved Sep. 8, 2005, from http://www.w3.org/TR/2004/WD-ws-chor-model-20040324/, 35 pages.

Waldspurger C. A. et al., "Spawn: A Distributed Computational Economy," May 1989, Xerox Palo Alto Research Center, pp. 1-32, 32 pages.

Web Services Architect, Web Services Resources, retrieved Nov. 6, 2003, from http://webservicesarchitect.com/resources.asp, 6 pages.

WestGlobal mScape™, Web Services Business Management System, retrieved Nov. 7, 2003, from http://www.westglobal.com/downloable_media/mscape_literature.zip, 18 pages.

Westglobal, Products—Overview, retrieved Nov. 7, 2003, from http://www.westglobal.com/products/mscape_overview.htm, 3 pages.

Westglobal, Products—Revenue Management Module, retrieved Nov. 7, 2003, from http://www.westglobal.com/products/mscape_revman.htm, 3 pages.

Xmethods website, retrieved Nov. 6, 2003, from http://www.xmethods.net/, 3 pages.

ZapThink, LLC, ZapThink Briefing Note—Oct. 8, 2002, retrieved Nov. 7, 2003, from http://www.grandcentral.com/assets/docs/GC.zapthink_report.pdf, 5 pages.

3$^{rd}$ Party Submission of Prior Art Under 37 CFR1.501, Oct. 22, 2012, 94 pages.

* cited by examiner

This service will allow anyone with a CSUF account to be billed for use of your application. On this page, please provide information about your application. ⎬ 201

Product Information

Please provide the information below. This is exactly what your customers will see when they purchase your application.

Company Name: [          ] ⎫
Product Name: [          ] ⎬ 203

Product Description [          ] ⎯ 205
*(Please enter plain text only)*

Redirect URL:
*(Please provide the URL that you would like to direct your customers to after they have provided us with their billing information)* [http://          ] ⎯ 207

---

Terms and Conditions (*Optional*)

If you wish, we can require all customers to agree to Terms and Conditions that apply to the use of your product before they purchase your product. If you would like to present Terms and Conditions, please enter them below. Otherwise, just leave this field blank. (*Please enter plain text only*) ⎬ 209

[          ]

Contact Information

Please provide your contact information for product related issues.
Contact email address: [          ] ⎫
Contact telephone number: [          ] ⎬ 211
Email address or URL for customers with product or technical inquiries: [          ] ⎭

*Fig. 2A*

225 {
Provide Pricing Information for Application AAA

Please follow these two steps to define Application AAA pricing:

1. Define the price you will charge for the dimensions on which Services used by the application are charged. For instance, if Application AAA uses Service EEE, you will define a price for *GB-Months of storage used* and *GB of data transferred*.

2. Optionally define a fixed, one-time fee, and/or monthly recurring fee.

Please define the prices in the tables below. On the next screen, you will be able to review the net proceeds you would obtain given the pricing defined below.

STEP 1: Application AAA for Service EEE

| Pricing Use Dimension & Amount Of Use | Application AAA Price | Service EEE Price | Optional Explanation of Pricing Dimension (e.g. *This is approximately 200 MP3s stored for a month*) |
|---|---|---|---|
| 227a GB-Month of storage used | $2.00 | $0.15 | |
| 227b GB of data transferred | $1.00 | $0.20 | |

STEP 2: Optional Application AAA Monthly and/or One-Time Fees

| | Pricing Use Dimension | Application AAA Price | Optional Explanation of Pricing Dimension (e.g. *This is a recurring monthly fee*) |
|---|---|---|---|
| ☐ | Monthly Fee | $0.00 | |
| ☑ | One-Time Fee | $10.00 | |

Click *Continue* to review Application AAA pricing.

Review Pricing Information for Application AAA

233 — The table below explains Application AAA net proceeds given the prices you entered and charges for each pricing use dimension of each service consumed by your users. Please review it and press the *Change* buttons if you want to amend your pricing.

Application AAA Price for Service EEE Pricing Use Dimensions  ( Change )

235

| Pricing Use Dimension & Amount Of Use | Application AAA Price | − | Service EEE Price | − | CSUF Charges (what's this?) | = | Application AAA Net Proceeds (what's this?) |
|---|---|---|---|---|---|---|---|
| GB-Month of storage used | $2.00 | | $0.15 | | $0.19 | | $1.66 |
| GB of data transferred | $1.00 | | $0.20 | | $0.08 | | $0.72 |

Optional Application AAA Monthly and/or One-Time Fees  ( Change )

237

| Pricing Use Dimension | Application AAA Price | − | CSUF Charge (what's this?) | = | Application AAA Net Proceeds (what's this?) |
|---|---|---|---|---|---|
| One-Time Fee | $10.00 | | $1.00 | | $9.00 |

Review the information below, then click "Place your order."

Product Information

Application AAA

Application AAA lets you store files over a network, making it easy to access from any computer just like a local hard drive. You can back up most file types, including photos, music, and office application documents.

Pricing

- $2.00 per GB-Month of storage used
  This is approximately 200 MP3s stored for a month.
- $1.00 per GB of data transferred
  This is equivalent to listening to approximately 150 MP3s.
- $5.00 Monthly charge
  A recurring monthly charge for the use of Application AAA.
- $10.00 One-time charge
  A one-time charge for the use of the Application AAA.

Note: CSUF will charge for your use of Application AAA on the 1st of every month.

Total due today

| | |
|---|---|
| Recurring Monthly charge: | $5.00 |
| One-time charge: | $10.00 |
| Total: | $15.00 |

Payment Method:
Visa: ***-11111
Exp: 02/2010

Billing Address:
John Smith
1111 1st St.
Seattle, WA 98144
United States
Phone: 1 (202) 555-1111

● Place your order — 313

Terms and Conditions

☐ Check here to indicate that you have read and agree to the terms of (1) CSUF Services Licensing Agreement, (2) the Application AAA terms of use, and (3) Service EEE terms of use. — 315

Review the information above, then click "Place your order."

● Place your order — 317

*Fig. 3C*

USING CONFIGURED APPLICATION PRICING TO DETERMINE END USER FEES FOR USE OF INVOCABLE SERVICES

CROSS-REFERENCE TO RELATED APPLICATIONS

This application is a divisional application of co-pending U.S. patent application Ser. No. 11/618,480, filed Dec. 29, 2006 and entitled "Using Configured Application Pricing To Determine End User Fees For Use of Invocable Services," which is hereby incorporated herein by reference. U.S. patent application Ser. No. 11/618,480 is related to co-pending U.S. patent application Ser. No. 11/618,469, filed Dec. 29, 2006 and entitled "Providing Configurable Pricing For Use Of Invocable Services By Applications," and to co-pending U.S. patent application Ser. No. 11/618,486 filed Dec. 29, 2006 and entitled "Providing Configurable Use By Applications Of Sequences Of Invocable Services," each of which is hereby incorporated by reference in its entirety.

TECHNICAL FIELD

The following disclosure relates generally to facilitating use of invocable services by applications in a configurable manner, such as to track use of third-party invocable services by applications on behalf of end users and to allocate fees charged end users between the applications and the services as configured by providers of the applications and services.

BACKGROUND

Various mechanisms exist to allow computers and executing software applications to interact. For example, remote procedure call ("RPC") protocols have long existed that allow a program on one computer to cause a program on another computer to be executed. In a similar manner, various object-oriented architectures such as CORBA ("Common Object Request Broker Architecture") and DCOM ("Distributed Component Object Model") provide remote execution capabilities. In addition, various middleware programs have been implemented to connect separate applications (often of distinct types and from unrelated sources) to allow communication. For example, various EDI ("Electronic Data Interchange") networks exist that provide standard mechanisms to allow a computer system of one user of the network to send data to a computer system of another user of the network.

The widespread popularity of the World Wide Web ("Web") has provided additional opportunities for computers to inter-communicate. For example, much current Web use involves users interactively requesting Web pages from Web servers (e.g., via Web browser applications executing on user computers) and receiving the requested information in response. In addition, there is also growing use of the Web to support the programmatic interaction of remote applications to exchange information via defined APIs ("application program interfaces"), such as via Web services. Web services allow heterogeneous applications and computers to interact, and can be defined and implemented using a variety of underlying protocols and techniques. For example, some Web service implementations return data in XML ("eXtensible Markup Language") format using HTTP ("HyperText Transport Protocol") in response to a Web service invocation request specified as a URI ("Uniform Resource Identifier"), such as a URL ("Uniform Resource Locator") that includes a specified operation and one or more query parameters. In other implementations, additional underlying protocols are used for various purposes, such as SOAP ("Simple Object Access Protocol") for standard message exchange, WSDL ("Web Services Description Language") for description of service invocations, and UDDI ("Universal Description, Discovery, and Integration service") for discovery of available services.

Although Web services and other mechanisms allow various applications and computers to interact, various problems exist with the use of such interaction mechanisms. For example, if a developer of an application would like to incorporate the use of fee-based Web services that are available from third parties in the application, but in a manner that end users of the application will be responsible for corresponding fees, such functionality is typically difficult and costly to implement. Such functionality may include, for example, mechanisms to collect specified payments from end users, and mechanisms to distribute payments to providers of the Web services used by the application. The functionality may also include mechanisms to allow the application developer to manage and monitor the use of third-party Web services via the application, to allow end users to monitor their own use of Web services via the application, etc. In addition, the application developer will typically be liable for the Web service usage costs to the third parties if payment is not ultimately obtained from the end users.

BRIEF DESCRIPTION OF THE DRAWINGS

FIGS. 2A-2D illustrate examples of interactions between application creators and an embodiment of a system that enables configuration of use of invocable services.

FIGS. 3A-3D illustrate examples of interactions between end users and an embodiment of a system that enables the end users to obtain access to invocable services via an application in accordance with configuration specified for the application.

DETAILED DESCRIPTION

Figure 1A:
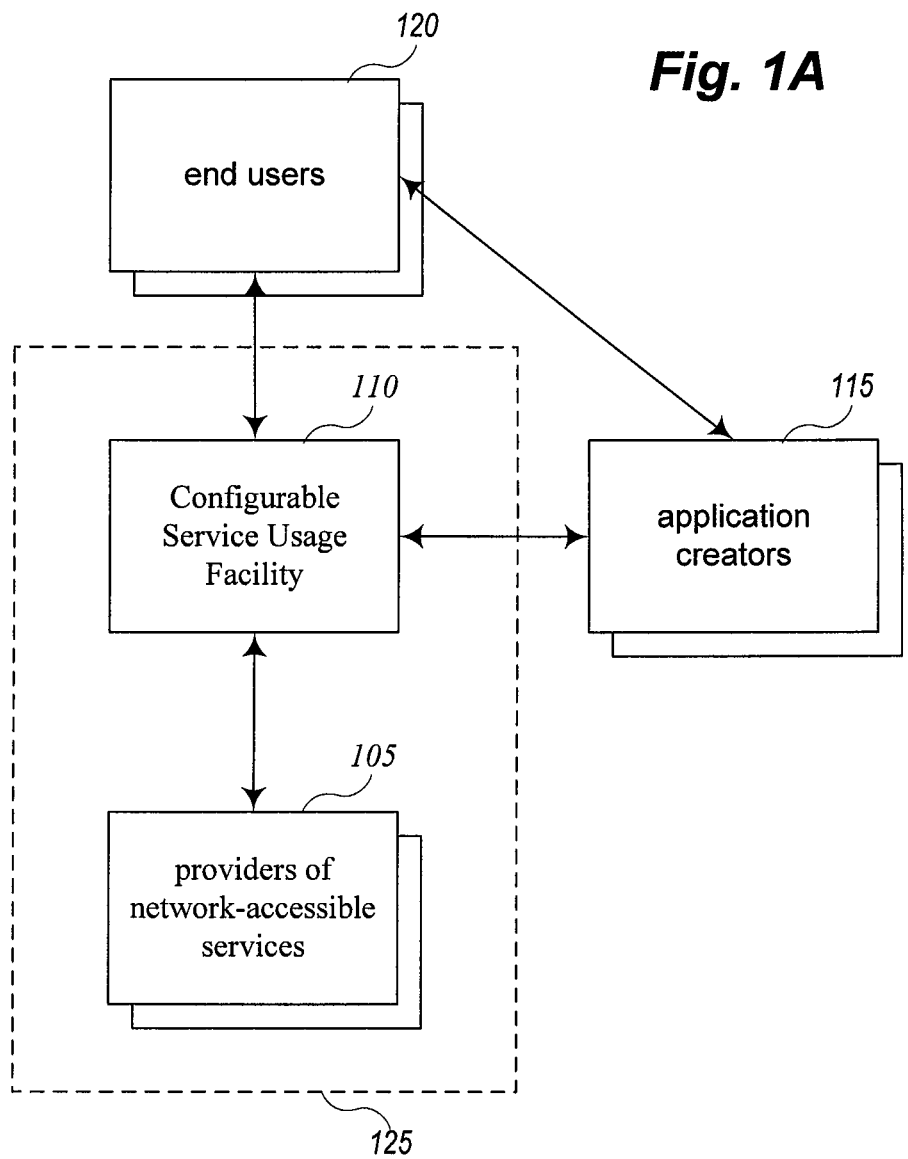
FIGS. 1A-1B illustrate examples of interactions to facilitate use of invocable services by applications in a configurable manner.

Techniques are described for facilitating use of invocable services by applications in a configurable manner. In at least some embodiments, the invocable services are Web services or other network-accessible services. In addition, in at least some embodiments the invocable services are fee-based services that are made available by providers of the services for use by others in exchange for fees defined by the service providers. The described techniques facilitate use of such invocable services by software applications in a manner configured by the developers of the applications. In at least some embodiments, the configuring of the software applications includes allowing the application developers to define pricing terms that will be used to determine fees that end users of the applications will be charged for use of the invocable services via the applications. In at least some embodiments, the described techniques are performed by an automated Configurable Service Usage Facility ("CSUF") system, as described in greater detail below.

In at least some embodiments, a user associated with an application (e.g., an application developer user or other application creator user that is involved in creation of the application) may interact with an embodiment of the CSUF system to configure pricing and other information for use of selected invocable services via the application. Types of applications that may use such invocable services may include, for example, application programs designed to execute on computing devices of end users, as well as server-based applications that end users may access using remote client devices (e.g., Web applications accessed via a Web browser executing on a client device of an end user).

To perform the configuration for an application, in at least some embodiments, an application creator user selects one or more invocable services that are available via the CSUF system, and interactively configures a usage model for each selected service to correspond to use of the service via the application. A configured usage model for a service may include a variety of pricing terms and other information related to use of the service, such as a configured indicated price for a configured indicated amount of use of a configured indicated use dimension (e.g., an indicated price for each use of the service, an indicated price per amount of time of use, an indicated price per unit of processing time, an indicated price per unit of storage used, an indicated price for a predetermined number of times of use in a predetermined period of time, etc.). In addition, in some situations a selected service may be a fee-based service that has a predefined usage model that specifies fees for use of the service, such as with pricing terms specified by a provider of the service. If so, the configured usage model for the service may differ from the predefined usage model for the service in one or more ways, such as by having a differing use price, a differing amount of use, and/or a differing use dimension.

After the application creator user has configured a usage model for each of one or more selected invocable services for an application, the CSUF system in some embodiments provides the application creator user with an application key (e.g., an alphanumeric string) for use by the application in order to facilitate tracking of the use of services by the application, while in other embodiments the application creator user may instead select the application key and provide it to the CSUF system (e.g., for use in situations in which the application development is completed and the application is already configured to use a particular application key). In particular, the application key is for use when an executing copy of the application makes use of one of the selected invocable services, such as by including the application key when an executing copy of the application makes a call to invoke or request access to one of the selected invocable services. When the application key is received by the CSUF system as part of the use of a selected invocable service, the application key may be used by the CSUF system to identify the application that used the service, and to track the use by that application. When appropriate (e.g., once a month, for each service usage, etc.), the configured usage model specified for use of the service by the application may be retrieved, and appropriate pricing terms may be determined from the configured usage model in order to determine fees to be charged an end user of the application copy for the use of the service.

In addition, in some embodiments, before an end user may access selected services via an executing copy of an application, the end user first subscribes to the use of those services via the application. In particular, the end user may be directed to interact with the CSUF system to perform the subscription, which may include providing payment information for fees to be charged to the end user, as well as optionally providing other information to the CSUF system (e.g., end user contact information, an indication of assent to any specified use terms and conditions for the application and/or the selected services, etc.). The end user may be directed to interact with the CSUF system at various times and in various ways in various embodiments, including when the end user is first purchasing or otherwise acquiring the application, when the end user first attempts to use the application, when the end user first attempts to use a selected service via the application, etc. In addition, in some embodiments, the end users are charged recurring fees (e.g., monthly fees) and/or one-time fees (e.g., setup fees). The recurring and/or one-time fees may be charged in advance (e.g., at a beginning of a month for which a monthly fee corresponds) and/or periodically after use has occurred (e.g., at the end of a month for any use in excess of a standard monthly charge during that month). Accordingly, an end user subscription may in some embodiments and situations be for recurring use of an application and service(s) (e.g., a monthly subscription that is automatically renewed unless otherwise specified), while in other situations may be for other types of use (e.g., for a single use, for use for only a limited specified time, for use for only a limited number of times, etc.).

After an end user subscribes to use of the selected services for an indicated application, in at least some embodiments a user token is provided for use with a copy of the application. In some embodiments, the end user may be provided with the user token, and then use the user token to customize or configure the application copy to be used by the end user (e.g., by supplying the user token to the application copy). In other embodiments, a user token may be associated with an application copy in other manners, such as if other software stores the user token and supplies it when appropriate for use with that application copy. For example, the other software may be a proxy server operated by the application provider that receives service usage requests from the application copy, and adds the user token or other corresponding user information when forwarding the service usage requests on to their destinations. The user token may have various forms in various embodiments, such as a random alphanumeric string associated with the end user, or an alphanumeric string that includes various information about the end user (e.g., an indication of the end user name and/or unique identifier, an indication of the application key for the application with which the user token may be used, an indication of a creation time and a subsequent time-to-live value during which the end user may use the user token, etc.) and that may be encoded to protect the included information (e.g., by being encrypted, by being the result of a one-way hash, etc.). The user token (or other user information based on the user token, such as a user credential, discussed below) may be used in a manner similar to the application key, such as by including the user information as part of a call by the end user's copy of the application to invoke or request access to one of the selected invocable services. When the user token or other user information is received by the CSUF system as part of the use of a selected invocable service, the user information may be used by the CSUF system to identify the end user on whose behalf the service use occurred (and if the user tokens are specific to the applications with which they are used, to identify the application that used the service), and to track the use by that end user. When appropriate (e.g., once a month, for each service usage, etc.), the payment information specified by the end user may be retrieved and used for providing payment for use of the service via the application, such as based on the configured usage model for the application.

As one particular example of end user interaction with the CSUF system, in some embodiments an application with one or more configured usage models for selected services receives not only an application key to be used as part of the application, but also a reference to the CSUF system to be used to facilitate subscriptions by end users (e.g., an Internet URL that directs an end user to the CSUF system). When an end user requests to purchase, subscribe to or otherwise acquire access to the application (e.g., by interacting with a Web site of the application creator), the end user is directed to the CSUF system to complete the subscription process and receive a user token. The end user acquires a copy of the application (e.g., by downloading the application copy from the Web site of the application creator), and supplies the user token to the acquired application copy, such as during an initialization process of the application copy, or instead at other times (e.g., when the end user first attempts to use application functionality that is based on capabilities of one of the selected services; periodically, such as if an end user is prompted to periodically supply new user tokens obtained from the CSUF system; etc.). When the application copy receives the user token, in some embodiments it interacts with an embodiment of the CSUF system to obtain a user credential based on the user token, such as by supplying the user token and other information related to an identity of the end user and/or a computing device of the end user on which the application copy will be used (e.g., a public key certificate or identity certificate, such as an X.509 certificate based on the Internet Engineering Task Force's Public-Key Infrastructure X.509 standard). After such a user credential is obtained from the CSUF system, it is then stored with the application copy, and used along with the application key to make service invocation calls or other requests to obtain access to selected invocable services. As previously noted, in some embodiments such user credentials may have a limited time-to-live, such that the end user and/or application copy may need to periodically obtain new user certificates from the CSUF system. Furthermore, in some embodiments a user credential may include additional information, such as information about use restrictions (e.g., that service invocations based on the user credential may occur only at certain times, only at certain volumes, etc.), which may then be enforced by the CSUF system, application copy and/or selected invocable services. In addition, in some embodiments the user credential is used to associate an application copy, end user and end user's computing device together, such that access to some or all of the functionality of the application copy may be available only to the end user and only on the end user's computing device.

Thus, both an application key and a user token (or a user credential based on one or both of them) may be supplied by an application when accessing invocable services on behalf of an end user. The use of the various invocable services on behalf of an end user is then metered (e.g., by tracking use based on the application key and/or the user token or credential) by the CSUF system or by an associated system, so that the end user may be charged appropriate fees for the use according to the configured usage model specified by the application creator for the application. The revenue collected based on the end user's use of the invocable service may be subsequently split between the application creator and the one or more service providers of the invocable services, such as if the configured usage model results in fees charged to the end user that are greater than fees charged by the providers of the invocable services. In some embodiments, if payment is not obtained from the end user for the use of invocable services, the application creator does not receive corresponding payment, but in some embodiments is also removed by the CSUF system of liability for fees charged by the providers of the invocable services for that use (and that does not owe any money to the service providers for use of the invocable services via the indicated application). In other embodiments, liability may not be removed in certain situations, such as if an application creator configures a use price for a selected invocable service that is less than the use price associated with the selected invocable service (or liability may be removed for only a portion of the use price associated with the selected invocable service, such as the use price configured by the application creator), if the application creator specifies a configured use price based on a use dimension that is not used by the selected invocable service, etc. Furthermore, in some embodiments and situations, the CSUF system may provide authentication functionality, such as in response to a request from an executing copy of an application to access a particular selected service on behalf of an end user. The authentication functionality may include determining whether the application and end user are authorized to access the particular selected service, such as by retrieving information regarding any configured usage models for the application and any subscription information for the end user, and/or by using information encoded in and/or associated with a received user credential or user token.

In some embodiments, invocable services may further charge fees for their use based on multiple different use aspects (e.g., by specifying use prices with respect to multiple use dimensions). For example, an invocable storage service may charge fees based on the amount of data stored (e.g., with a first indicated price per megabyte of data) and on the number of times that storage and/or retrieval access occurs (e.g., with a second indicated price per access). Similarly, an application creator user may configure pricing terms that correspond to multiple use dimensions for an invocable service, whether based on the same multiple use dimensions as specified by the invocable service or not (e.g., by adding a use price for a second use dimension when the underlying invocable service specified a price for only a single use dimension). If an application creator user specifies one or more custom use dimensions for an invocable service that differ from the use dimensions specified by the service, the application may further in some embodiments provide information to the CSUF system during application execution to specify how much usage has occurred with respect to those custom use dimensions.

In addition, in some embodiments the CSUF system may charge various fees for the functionality that it provides. For example, the CSUF system may charge a fee to an application creator for providing capabilities to allow the application creator to specify one or more configured usage models for selected invocable services, for providing capabilities to meter usage of invocable services and obtain corresponding payment from end users, for providing capabilities to pay service providers for use of their services based on corresponding payments received from end users, etc. Furthermore, the fees charged may have various forms, such as a predetermined percentage (e.g., 10%) of the proceeds after paying service provider(s) for use of their service(s), a predetermined amount for each service (e.g., $0.50), etc., or a combination thereof. Additional details related to configuring prices and allocating fees between application creators or other application providers, service providers, and an entity providing an embodiment of the CSUF system are included with respect to a described Configurable Service Sequence Usage Facility system in U.S. patent application Ser. No. 11/618,486, filed concurrently and entitled "Providing Configurable Use By Applications Of Sequences Of Invocable Services," which is hereby incorporated by reference in its entirety.

As previously noted, the described techniques may be used in various manners in various embodiments. For example, the CSUF system may be used with various types of applications, such as applications with a graphical user interface (e.g., desktop applications or Web applications), a command-line interface (e.g., for a system utility), or a programmatic interface. Similarly, the invocable services may be of various types, including, but not limited to, Web services, storage services, indexing services, and queuing services. In addition, some or all of the invocable services may be provided by an entity providing the CSUF system and/or by third-party service providers.

FIG. 1A illustrates an example of interactions in which application creator users configure usage models for invocable services to be used via their applications, and in which end users subsequently subscribe to use those services via those applications. In this example, the invocable services (also referred to as "component services") are network-accessible services, such as Web services or other services that may be remotely invoked or otherwise accessed over one or more computer or transmission networks. In particular, providers of network-accessible services 105 each offer one or more component network-accessible services (not shown) as being available to third-party applications via the Configurable Service Usage Facility ("CSUF") system 110, with each component service having predefined pricing terms (not shown) that include an indicated use price for an indicated amount of use with respect to an indicated use dimension. In some situations, some or all of the providers of the network-accessible services may be the same entity that provides the CSUF system, with the CSUF system 110 and the provider systems 105 being part of a group of systems 125 of that entity, while in other embodiments some or all of the providers of the network-accessible services may be distinct from and external to the entity that provides the CSUF system.

After the component network-accessible services are specified to the CSUF system, an application creator user 115 interacts with the CSUF system to select one or more of the component services to use in an application being created (not shown), and configures one or more usage models (not shown) for the selected services. After the usage model(s) are configured, the application creator receives an application key for use with the application, as well as one or more URLs to use to direct end users to the CSUF system to perform subscription activities regarding the application. The application key may in some embodiments be any unique identifier, such as an alphanumeric string of a predetermined length. In addition, the application creator may associate the application key with the application in various ways, such as by configuring the application to use the application key when making requests to use other selected services.

After the application creator 115 develops the application and configures the usage models, an end user 120 may decide to purchase or otherwise acquire access to the application, such as by interacting with the application creator's Web site (not shown) or in other manners (e.g., via other Internet sites, such as a Web site associated with the CSUF system). The end user 120 then interacts with the CSUF system 110 to subscribe to use of the selected services via the application, such as by providing contact and payment information. The end user then receives a user token for use with a copy of the application, which may be any unique identifier (such as an alphanumeric string of a predetermined length). After using the user token to configure a copy of the application, such as based on a corresponding user credential, the end user 120 may use the application copy to access the network-accessible services.

Figure 1B:
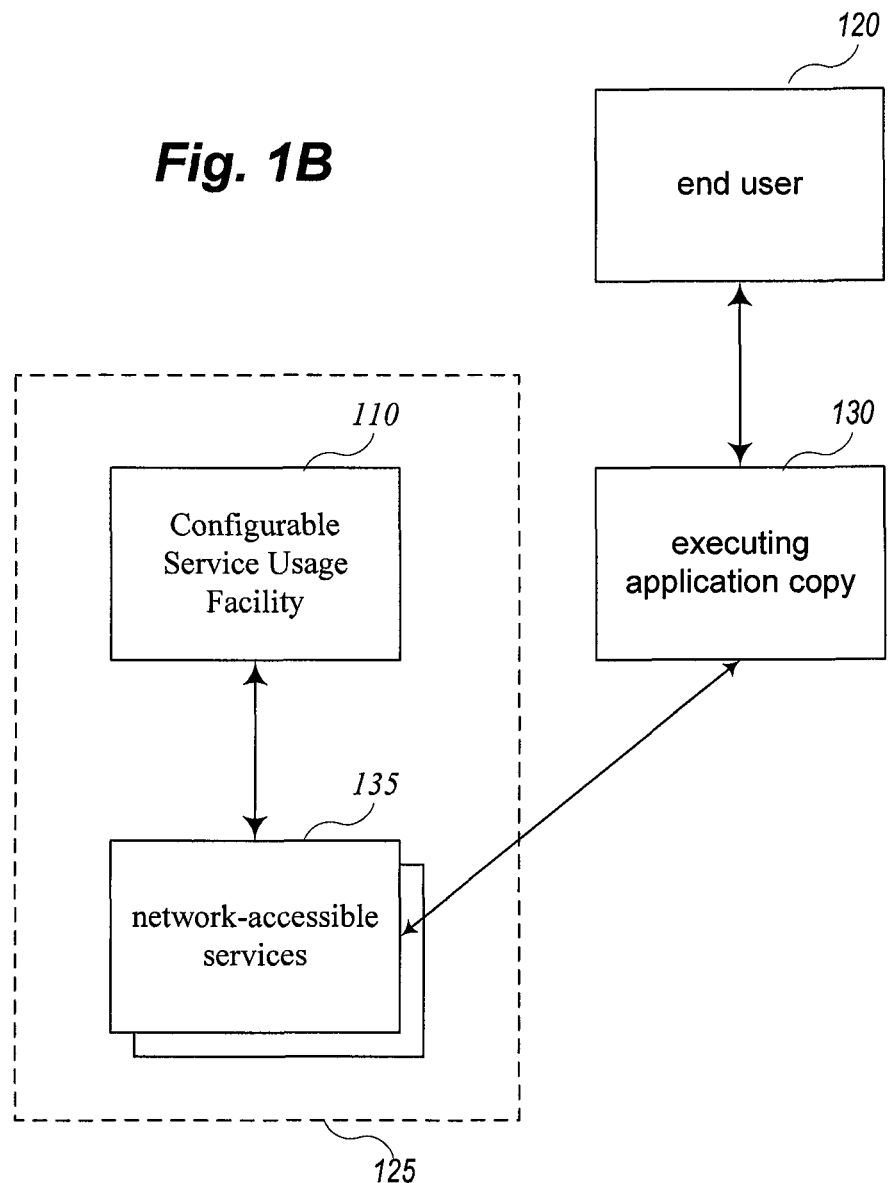

FIG. 1B illustrates an example of interactions between an end user, an executing application copy, one or more selected invocable services and the CSUF system as the application copy invokes the selected invocable services on behalf of the end users. In particular, in this example, an end user 120 is interacting with an executing application copy 130, such as an application created by one of the application creators 115 of FIG. 1A and provided to the end user by the one application creator or other application provider (e.g., a distributor of the application). The application copy 130 includes an application key (not shown) based on prior configuration of one or more usage models via the CSUF system 110 for the application, and has been configured based on a user token (not shown) for the end user in order to obtain a corresponding user credential, such as previously described with respect to FIG. 1A.

During execution, the application copy 130 invokes one or more network-accessible services 135 on behalf of the end user, such as network-accessible services provided by the providers 105 of FIG. 1A. When invoking a network-accessible service, the application copy provides its application key and the user credential. In this example, when network-accessible services receive invocation requests from the application copy, some or all of the network-accessible services may authenticate the requests by sending to the CSUF system the received application key and user credential, as well as an identifier associated with the network-accessible service. If so, such network-accessible services may provide their capabilities to the application copy only if the requests are authenticated by the CSUF system 110. If an invocation request of a network-accessible service is authenticated, or if such authentication is not performed, the network-accessible service may then perform a requested task and return results (not shown) to the application copy. When the application copy receives results from a network-accessible service, the results may be indicated to the end user or otherwise used by the application copy as appropriate.

Furthermore, in at least some embodiments, the network-accessible services may also interact with the CSUF system 110 to indicate the use of the network-accessible service by the application copy 130 on behalf of the end user 120 (e.g., by providing the received application key, received user credential, and service identifier), such as to enable service use metering capabilities of the CSUF system. Various information may be sent to the CSUF system by the network-accessible service, including information regarding the amount of use of the service with respect to one or more use dimensions specified in a predefined usage model for the service. In at least some embodiments, some or all of the network-accessible services may perform a single interaction with the CSUF system that enables both authentication and metering capabilities, such as before the service functionality is provided if the amount of use of the service that will occur can be determined in advance. In other embodiments, the CSUF system may provide metering capabilities by initiating communication with some or all of the network-accessible services periodically to determine prior and/or current use of the service on behalf of the end user, such as to track the amount of storage that is currently used by an end user and application copy for a storage service. In yet other embodiments, the application copy may instead interact with the CSUF system (or an associated system acting as an intermediary) to invoke some or all of the network-accessible services. In those embodiments, authenticating may happen before the network-accessible service is invoked on behalf of the end user, and results may be returned to the application copy via the CSUF system or directly to the application copy by the network-accessible services.

Authentication of an access request to an indicated network-accessible service by the application copy on behalf of the end user may be performed in various ways in various embodiments. For example, authentication may include verifying that the user credential (or user token) is currently valid, that the application key is valid, and that use restrictions (if any) that are associated with or embedded with the user credential are satisfied. The authentication functionality may further include retrieving information about the application and end user to determine whether the access to the indicated service is authorized, such as by retrieving information regarding any configured usage models for the application and any subscription information for the end user. In at least some embodiments, a user credential (or user token) may be revoked or expire for various reasons, such as the end user canceling a subscription to an application, payment not being obtained for use of a service, a predefined life of the user credential being reached (e.g., based on a specified time-to-live value), etc. In those embodiments, service invocation authentication may occur each time that a network-accessible service is invoked. In other embodiments, some or all of the calls to a network-accessible service may not be individually authenticated (or may only be partially authenticated, such as by only verifying the user token or user credential), such as additional calls within a predetermined period of time to a particular network-accessible service from a single application copy on behalf of the same end user, or for calls to the component service from a predetermined set of computing systems (e.g., based on their IP address).

Various information about the use of an indicated service that is received by the CSUF system may be stored for later use in determining fees to be paid by end users for use of network-accessible services via an application. In at least some embodiments, the information may include the user credential (or user token), the application key, an indication of the service used, and an indication of the amount of use of the indicated service with respect to an indicated use dimension. In addition, in at least some embodiments, an application copy may interact with the CSUF system to provide metering information with regard to one or more use dimensions other than the predefined use dimensions of the component service. If so, the use of the component service with respect to the predefined use dimension may nonetheless be metered by the CSUF system, such as for use in determining fees to be paid to the service provider for the use of the service.

As previously mentioned, when appropriate (e.g., once a month, for each service usage, after a predetermined amount of fees are owed, when canceling a subscription, etc.), fees to be charged to an end user for the use of one or more network-accessible services via one or more applications are determined. The determination of such fees may include retrieving information about the configured usage model(s) specified for use of the services via the applications. Other fees (e.g., recurring application use fees, or fees paid by the end user to the CSUF system) may also be determined and added to the fees owed by the end user based on the service usage. Payment may be obtained using supplied payment information from the end user. If obtaining payment was not successful, in some embodiments various remedial actions are taken, such as contacting the end user to obtain alternative payment information and/or to prevent future access to the network-accessible services by the application (e.g., by revoking the user credential or the user token so that it will no longer be authenticated).

After receiving payment of fees from the end user, the CSUF system may allocate the fees received between the provider of the application copy and the providers of the network-accessible services used by the application, and initiate payment of the allocated amounts to the parties. In some embodiments, the service provider of each component service used by the application is paid according to the use of the service by the application on behalf of the end user (based on the predefined usage models for the services), and the application provider is paid the remaining fees. In at least some embodiments, the CSUF system may also allocate at least some of the fees to itself for the functionality that it provides, and if so the net proceeds received by the application provider and/or service providers may be reduced appropriately.

In at least some embodiments, an application creator or provider user associated with an application may interact with the CSUF system to monitor (e.g., in substantially real-time) use of network-accessible services via the application and/or to monitor fees to be paid to the application creator or provider. Similarly, in at least some embodiments, an end user may interact with the CSUF system to monitor use of an application by the end user and/or use of invocable services by the application on behalf of the end user, as well as to monitor any fees owed based on such use. In addition, application creator/provider users and end users may interact with the CSUF system to update various information about their applications and subscriptions as appropriate.

While not illustrated, some parties may serve multiple roles. For example, an application creator may also provide one or more component services that are available via the CSUF system. As another example, in some embodiments the entity providing the CSUF system may also create one or more applications. In addition, some of the parties may be an entity (e.g., a company) instead of an individual.

For illustrative purposes, some embodiments are described below in which specific embodiments of the CSUF system provide various specific types of capabilities with respect to various types of applications and network-accessible services, including using specific types of user interfaces and other interactions. However, it will be appreciated that the described techniques may be used in a wide variety of other situations, including with other types of computer-implemented services, with other types of applications, with other types of user interactions, etc., and that the invention is not limited to the exemplary details provided.

Figure 2B:
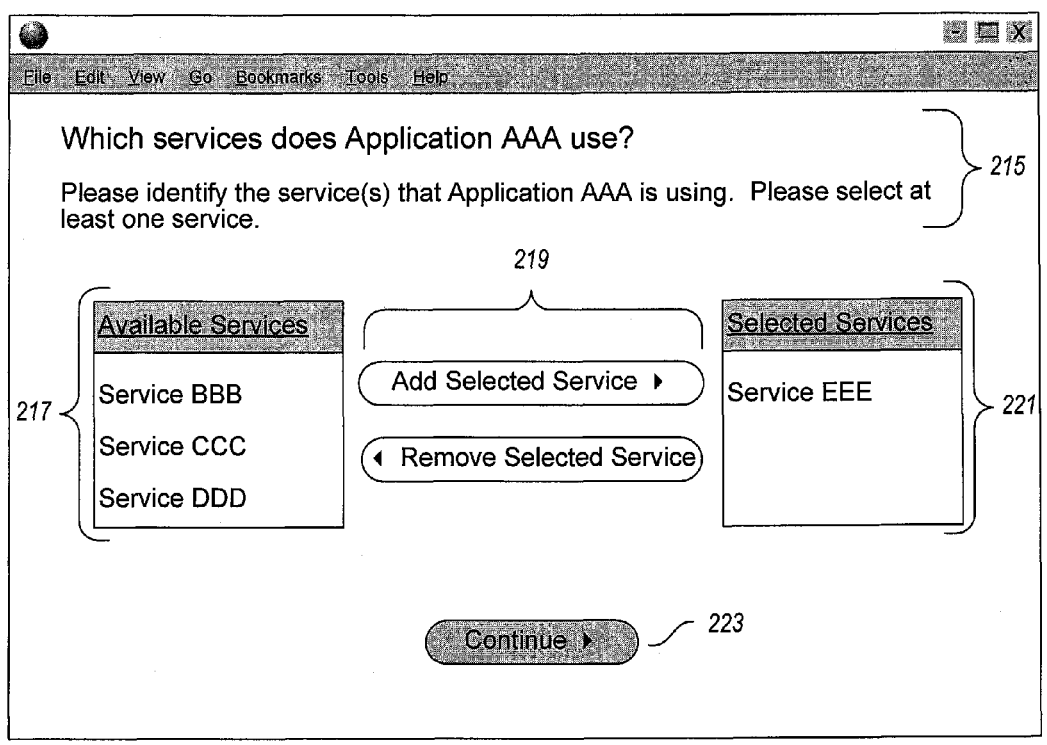

FIGS. 2A-2D illustrate examples of interactions between an application creator user and an embodiment of a CSUF system in order to configure a usage model for a selected component service to be used by an application being developed by the application creator user. In particular, FIG. 2A illustrates an example user interface screen that may be displayed to an application creator user to enable the application creator user to specify various information related to an application. In this example, the displayed information includes instructional information 201 for the application creator, a section 203 in which the application creator user can specify the name of the provider of the application and the name of the application, a section 205 to provide a description of the application, a section 207 to indicate a URL to redirect end users to after they have subscribed to use of the selected component services via the application, a section 209 to provide terms and conditions, and a section 211 to provide contact information for the application creator. In some embodiments, some or all of the contact information entered in section 211 is for use by the entity providing the CSUF system, and is not supplied to end users. After the application creator user enters the appropriate information in FIG. 2A, the information is submitted to the CSUF system by selection of a user-selectable control (not shown).

Next, in this example, the application creator user is presented with the user interface screen illustrated in FIG. 2B, to enable the application creator user to select one or more network-accessible services for use by the application of the application creator user. In particular, FIG. 2B includes an informational section 215, a list 217 of available services for the application, a list 221 of selected services for the application, user-selectable controls 219 for selecting and deselecting one or more services, and a user-selectable control 223 to submit the list of the selected services to the CSUF system. Additional information may be available for each of the available services in some embodiments, such as a description of the service, predefined pricing information, ratings or other assessment information, etc. Although only one component service is selected in this example, multiple component services, including multiple component services from different parties, may be used by an application.

Once the application creator user selects the one or more component services and uses the user-selectable control 223 to submit the selected services to the CSUF system, the user interface screen illustrated in FIG. 2C is presented to the application creator user. In this example, the selected service has a single usage model that includes predefined pricing information for two use dimensions, but in other embodiments a service may have multiple alternative usage models that the application creator may choose from (e.g., different usage models corresponding to different quality of service levels). In this example, FIG. 2C includes an information section 225, a section 227 for configuring the use prices for a component network-accessible service, a section 229 for configuring optional recurring (e.g., monthly) and/or one-time fees, and a user-selectable control 231 for submitting the configured usage model to the CSUF system. In this example, the information specified in sections 227 and 229 will be part of the configured usage model for the selected service and the application, although in other embodiments additional types of information may be specified (e.g., service-specific use restrictions, service-specific terms and conditions, etc.) and/or some of the illustrated types of information may not be available to be specified. If multiple component services had been selected, similar information would be displayed to the application creator user for each of the services.

In this example, section 227 includes rows 227a and 227b, with each row corresponding to one of the use dimension specified in the predefined pricing information for the selected service. The predefined pricing information is shown for each use dimension, including a predefined use price for a predetermined amount of use with respect to the use dimension. User-specifiable fields are also present to allow the application creator user to specify a distinct configured use price for the same predetermined amount of use with respect to the use dimension. While not illustrated here, in some embodiments, the application creator user may further be able to configure differing amounts of use and/or use dimensions. In this example, the application creator user may further specify an optional explanation, which will be provided to end users during configuration to explain the configured pricing. Accordingly, since multiple applications may each configure different usage models for those applications' use of a single component service, an end user using multiple such applications may be charged different fees for use of the same component service.

Although not shown, in some embodiments additional information may be specified for the configured usage model. For example, in some embodiments an application creator user may configure one or more use restrictions, such as to restrict a minimum or maximum use of a component service, and/or to restrict the use of the service to a particular type of use (e.g., non-commercial use). In some embodiments, some or all of the use restrictions of the component service are automatically incorporated as use restrictions for the application. As a second example, the application creator may be able to specify particular aspects of billing, such as the billing cycle, or the smallest increment in which to bill (e.g., in tenths of a GB/month).

After the application creator user selects user-selectable control 231 to define the configured usage model for the selected service, the application creator user is presented with the example user interface screen of FIG. 2D to confirm the configured usage model. In particular, FIG. 2D includes an informational section 233, a section 235 with the configured use prices, a section 237 with additional fees for use of the application, and a user-selectable control 239 to continue. In this example, sections 235 and 237 each contain a user-selectable control to allow the application creator user to make changes if so desired. In this example, the CSUF system charges a fee for providing its capabilities (e.g., 10% after paying the service provider for use of the component service), and sections 235 and 237 indicate that CSUF system fee as well as the portion of the fees from the end user that will be provided to the service provider and the application creator user (or a separate provider of the application that the application creator user represents).

Figure 3A:
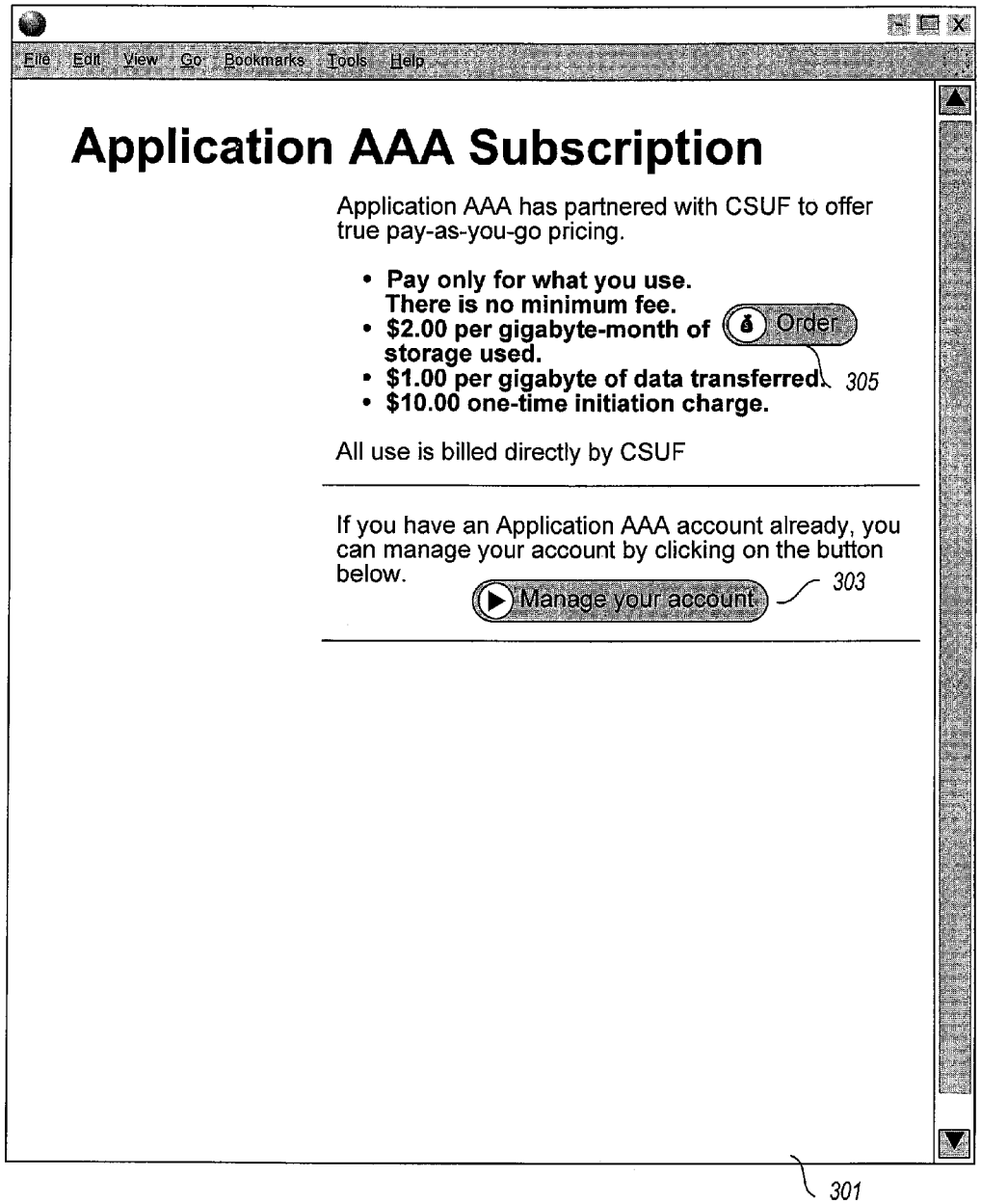

After the application creator user selects user-selectable control 239, the application creator will receive an application key for use with the application, as well as one or more indicated URLs to use to allow end users to interact with the CSUF system to subscribe to the application and its use of the selected service. The application key and the URLs may be provided to the application creator in various manners, such as by email or displayed on a user interface. The application creator may use the URLs in various ways, such as on the application creator's Web site (e.g., as shown in FIG. 3A), or instead as part of the application (e.g., to allow end user subscription to the application via an executing copy of the application).

The previously illustrated user interfaces are provided for example purposes, and the same or related functionality may be performed in other manners in other embodiments. For example, in other embodiments, more or less information may be displayed to an application creator user and/or obtained from an application creator user. Additionally, some or all of the information may be provided to an application creator user and/or obtained from an application creator user in other manners, such as programmatically rather than via a graphical user interface, or via the use of a custom application rather than via a Web-based interface.

After an application has been created by an application creator user and configured usage models have been specified for any selected component services, end users may subscribe to use the application and the functionality provided by any such component services. FIGS. 3A-3D illustrate examples of interactions between end users and an embodiment of the CSUF system in order to perform such a subscription process. In other embodiments, end users may obtain access to use such an application in a manner other than via a subscription, such as based on payment of a one-time fee or in other manners. In this example, FIG. 3A illustrates an example user interface screen 301 on an application creator's Web site, with the screen providing information to a potential end user about a particular application. This example screen further allows the end user to purchase access to the application or manage an existing subscription to the application. In particular, in this example the user interface screen includes user-selectable controls to "Order" 305 access to the application and to "Manage Your Account" 303. Information about the application on the user interface screen includes an overview about pricing for use of the component services via the application, a description of the application, and a name of the application. Additional information may be displayed in other embodiments, such as minimum system requirements and operating systems supported (e.g., for a desktop application that will be executed on the end user's computing system).

Figure 3B:
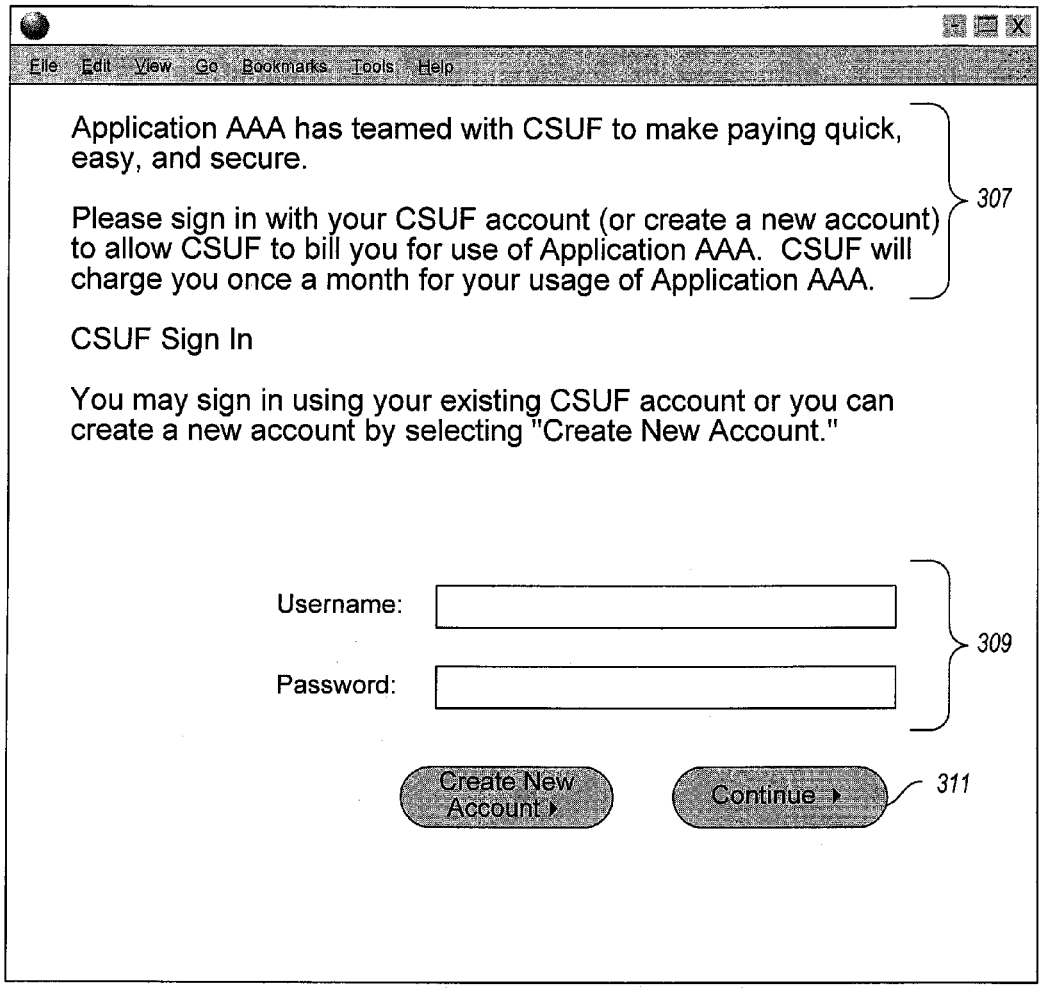
Figure 3D:
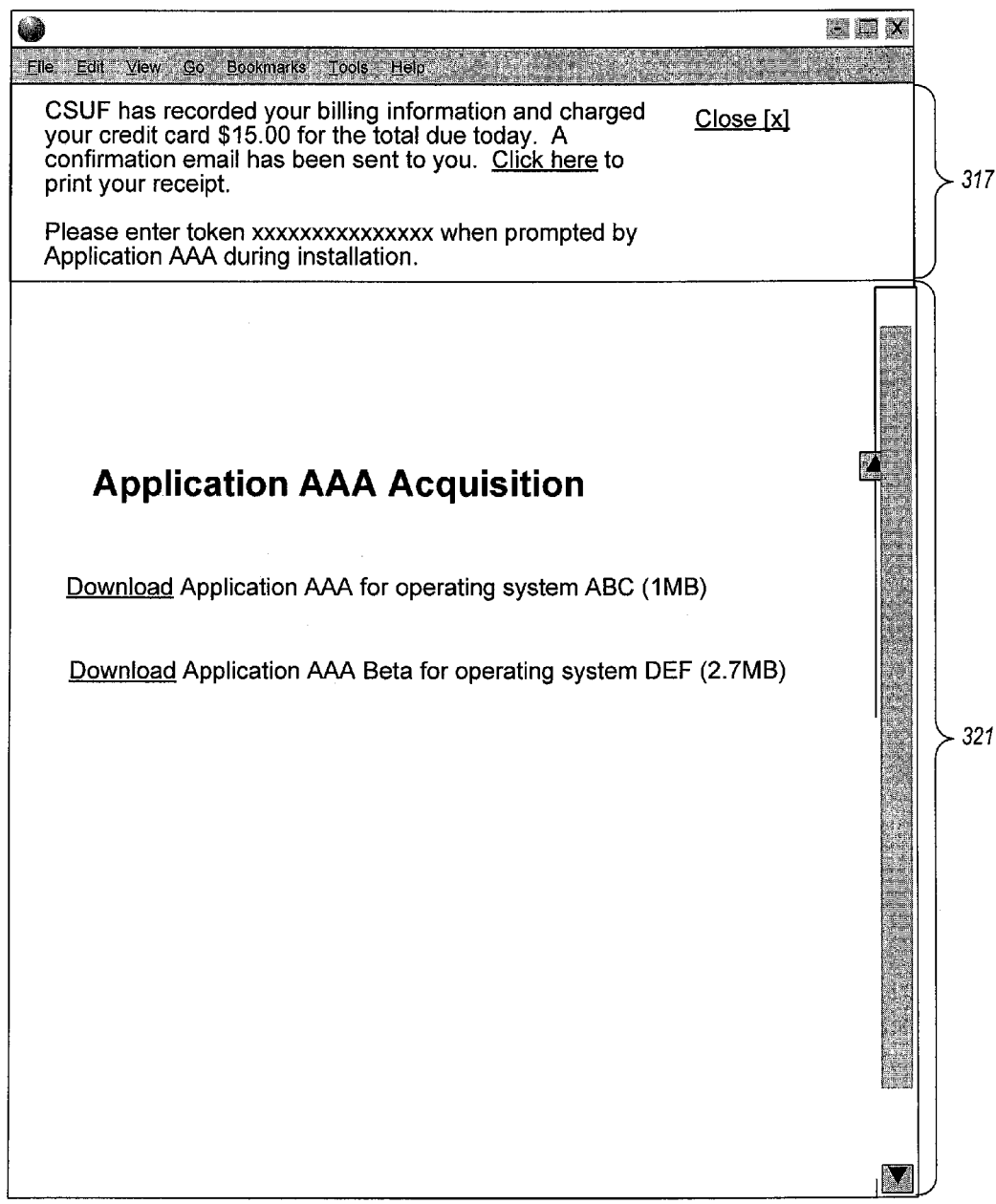

If the end user has not previously subscribed to the application and selects the "Order" user-selectable control 305, the end user is presented with the user interface illustrated in FIG. 3B. FIG. 3B illustrates an example sign-in page for the end user that is provided by the CSUF system, and may in some embodiments correspond to a URL supplied by the CSUF system to the application creator when configuring a usage model for the application. In this example, FIG. 3B includes an instructional information section 307, a section 309 for the end user to specify a username and password, and a user-selectable control 311 to continue the subscription process. The end user may create a new user account with the CSUF system, or in this example, is able to use a username and password for an account on an associated system if one already exists. If the end user is creating a new user account, the end user may be prompted to provide various types of information (e.g., payment information), which is not shown here. In addition, while not illustrated here, in some embodiments the CSUF system may gather information from the end user for one or more component services, such as to be supplied to the provider(s) of those component service(s).

After the end user has specified the various types of information for a new user account, or if the end user signs in to an account for which such information is already available, the user interface screen 313 of FIG. 3C is displayed to the end user. The user interface screen 313 provides information to the end user regarding the configured usage model for the application, and allows the end user to place an order for a subscription for access to the application and the one or more invocable component services used by the application. In particular, FIG. 3C includes various information about fees charged by the configured usage model (e.g., setup fees and recurring monthly fees), and about end user payment information that may be used to pay the fees. In this example, the information about the configured usage model for the application includes the configured use price for each of the use dimensions for the component services. In addition, in this example FIG. 3C includes a section 315 for the end user to agree to terms and conditions, such as terms and conditions specified by the CSUF system, by the application (e.g., as specified in section 209 of FIG. 2A), and/or by one or more of the component services. However, in other embodiments, the end user may have agreed to some of those terms and conditions at other times, or no such terms and conditions may be used. In addition, while the end user paid for the application subscription using a credit card in this example, various other payment methods (e.g., an ACH transaction, a debit card, a gift card) may be used in other embodiments.

After reviewing the information displayed in FIG. 3C, the user may proceed with the subscription process by selecting the "Place Your Order" user-selectable control 317. In this example, after appropriate processing by the CSUF system (e.g., checking that the end user has agreed to the terms and conditions, charging the end user for the setup fees and any recurring monthly fee, etc.), the user is presented with the example user interface screen illustrated in FIG. 3D. In this example, the user interface screen of FIG. 3D contains a receipt section 317 corresponding to the description, and a section 321 (e.g., based on the URL specified in section 207 of FIG. 2A) with information to enable the end user to download the application. The receipt section 317 in this example indicates a user token for the end user to use with the application, although in other embodiments the user token may instead be supplied in other manners (e.g., in a file included with a copy of the application download). In addition, in this example, a receipt was also sent via email to the end user. The section 321, in this example, includes user-selectable controls to allow the end user to download a copy of the application, so that the downloaded application copy may be used by the end user.

As with the example user interfaces for use in configuring usage models, the illustrated user interfaces for end user subscription are provided for example purposes, and the same or related functionality may be performed in other manners in other embodiments. For example, in other embodiments more or less information may be displayed to an end user and/or obtained from an end user. Additionally, some or all of the information may be provided to an end user and/or obtained from an end user in other manners, such as programmatically rather than via a graphical user interface, or via the use of a custom application rather than via a Web-based interface.

Figure 4:
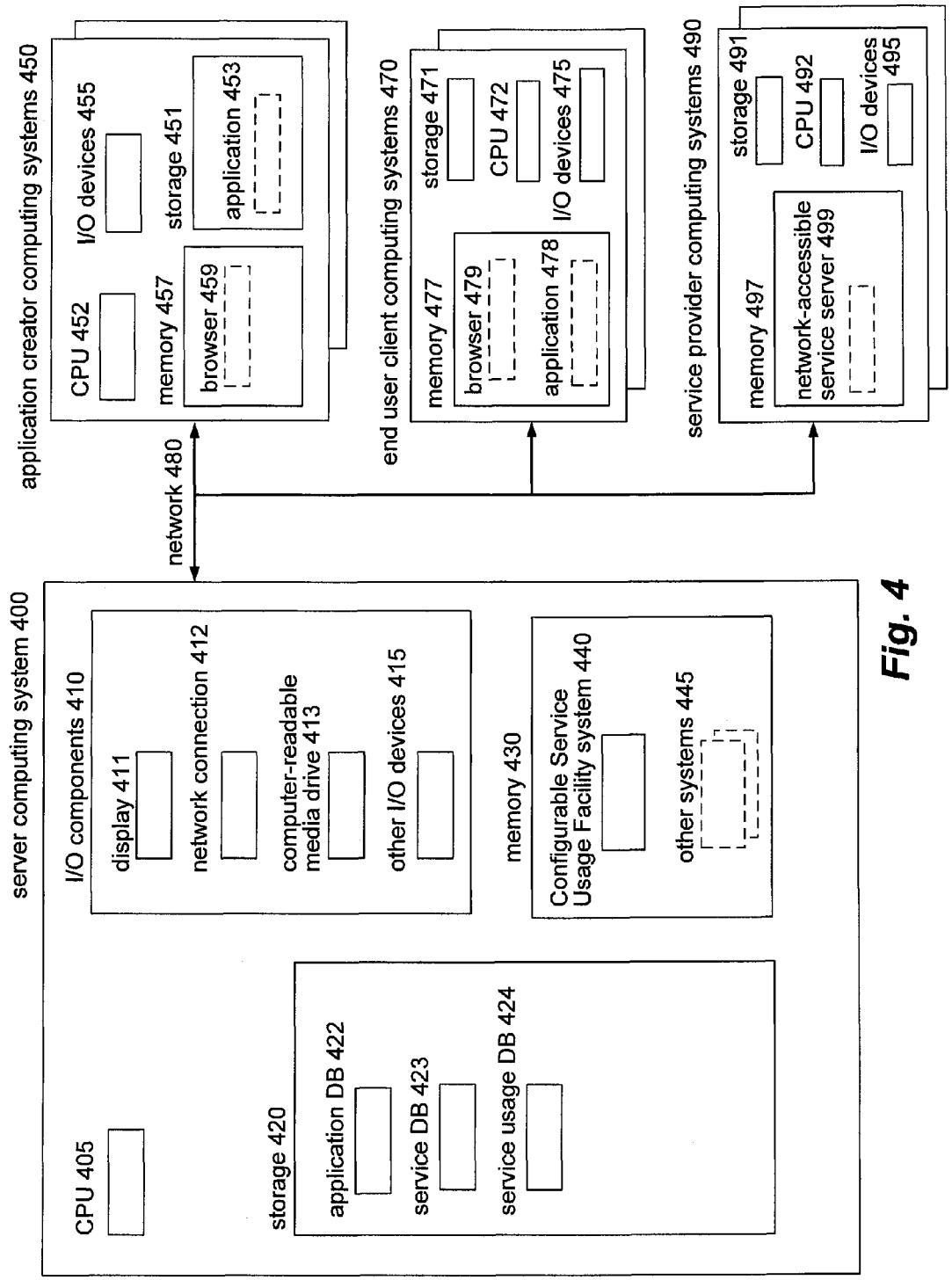
FIG. 4 is a block diagram illustrating a computing system suitable for executing an example embodiment of a system for facilitating use of invocable services by applications in a configurable manner.

FIG. 4 illustrates a server computing system 400 suitable for executing an embodiment of the Configurable Service Usage Facility ("CSUF") system, as well as various other computing systems. In this example, the other computing systems include one or more application creator computing systems 450, one or more end user client computing systems 470, and one or more service provider computing systems 490. In the illustrated embodiment, the server computing system 400 includes a CPU 405, various I/O components 410, storage 420, and memory 430. The I/O components include a display 411, a network connection 412, a computer-readable media drive 413, and other I/O devices 415 (e.g., a keyboard, a mouse, speakers, etc.).

An embodiment of the CSUF system 440 is executing in memory 430, and it interacts with the other computing systems over the network 480 (e.g., via the Internet and/or the World Wide Web, via a private cellular network, etc.). The other computing systems may similarly execute various software as part of the interactions. For example, a Web browser 459 executing in memory 457 of an application creator computing system allows an application creator user to interact with the CSUF system (e.g., to configure usage models for component services used by their applications and/or to monitor use of their applications). In addition, a Web browser 479 executing in memory 477 of an end user client computing system allows end users to interact with the CSUF system (e.g., to subscribe to an application). Furthermore, a network-accessible service server 499 may execute in memory 497 of a service provider computing system in order to provide a network-accessible service that is registered with the CSUF system and used by one or more applications.

In this illustrated embodiment, an application creator user creates an application 453 that is stored on storage 451 of the application creator computing system, and that is configured to use one or more invocable component services via the CSUF system that are provided by one or more service provider computing systems. One or more of the end users may then obtain a copy 478 of the application 451, such as based on interactions with the application creator computing system, and execute the application copy in memory 477 of the end users' computing systems (e.g., to provide various functionality via the selected services) after the end user has completed a corresponding subscription process via the CSUF system. In the illustrated embodiment, a variety of database data structures 422, 423 and 424 are present on the storage 420 for use by the CSUF system, such as to store information about applications and their configured usage models, about component services and their predefined usage models, and about tracked usage of applications and component services, although in other embodiments some or all such databases may instead be located elsewhere and/or be organized in other manners. Furthermore, in other embodiments the stored information may be stored in other manners. In addition, one or more optional other systems 445 may also be executing on the server computing system, such as an electronic marketplace system for network-accessible services.

It will be appreciated that the illustrated computing systems are merely illustrative and are not intended to limit the scope of the present invention. The computing systems 400, 450, 470 and/or 490 may instead each include multiple interacting computing systems or devices, and those computing systems may be connected to other devices that are not illustrated, including through one or more networks such as the Internet, via the Web, or via private networks (e.g., mobile communication networks, etc.). More generally, a server or client computing system or device may comprise any combination of hardware or software that can interact, including (without limitation) desktop or other computers, network devices, PDAs ("Personal Digital Assistants"), cellphones, wireless phones, pagers, electronic organizers, Internet appliances, television-based systems (e.g., using set-top boxes and/or personal/digital video recorders), and various other consumer products that include appropriate inter-communication capabilities. In addition, in some embodiments, at least some of the described functionality may instead not be provided as part of an embodiment of the CSUF system and/or other additional functionality may be available.

It will also be appreciated that, while various items are discussed or illustrated as being stored in memory or on storage while being used, these items or portions of them may be transferred between memory and other storage devices for purposes of memory management and data integrity. Alternatively, in other embodiments some or all of the software systems may execute in memory on another device and communicate with the illustrated computing systems via inter-computer communication. Some or all of the systems and/or data structures may also be stored (e.g., as software instructions or structured data) on a computer-readable medium, such as a hard disk, memory, a network, or a portable media article (e.g., a DVD or a flash memory device) to be read by an appropriate drive or via an appropriate connection. The systems and data structures may also be transmitted via generated data signals (e.g., by being encoded in a carrier wave or otherwise included as part of an analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). Such computer program products may also take other forms in other embodiments. Accordingly, the present techniques may be practiced with other computer system configurations.

Figure 5:
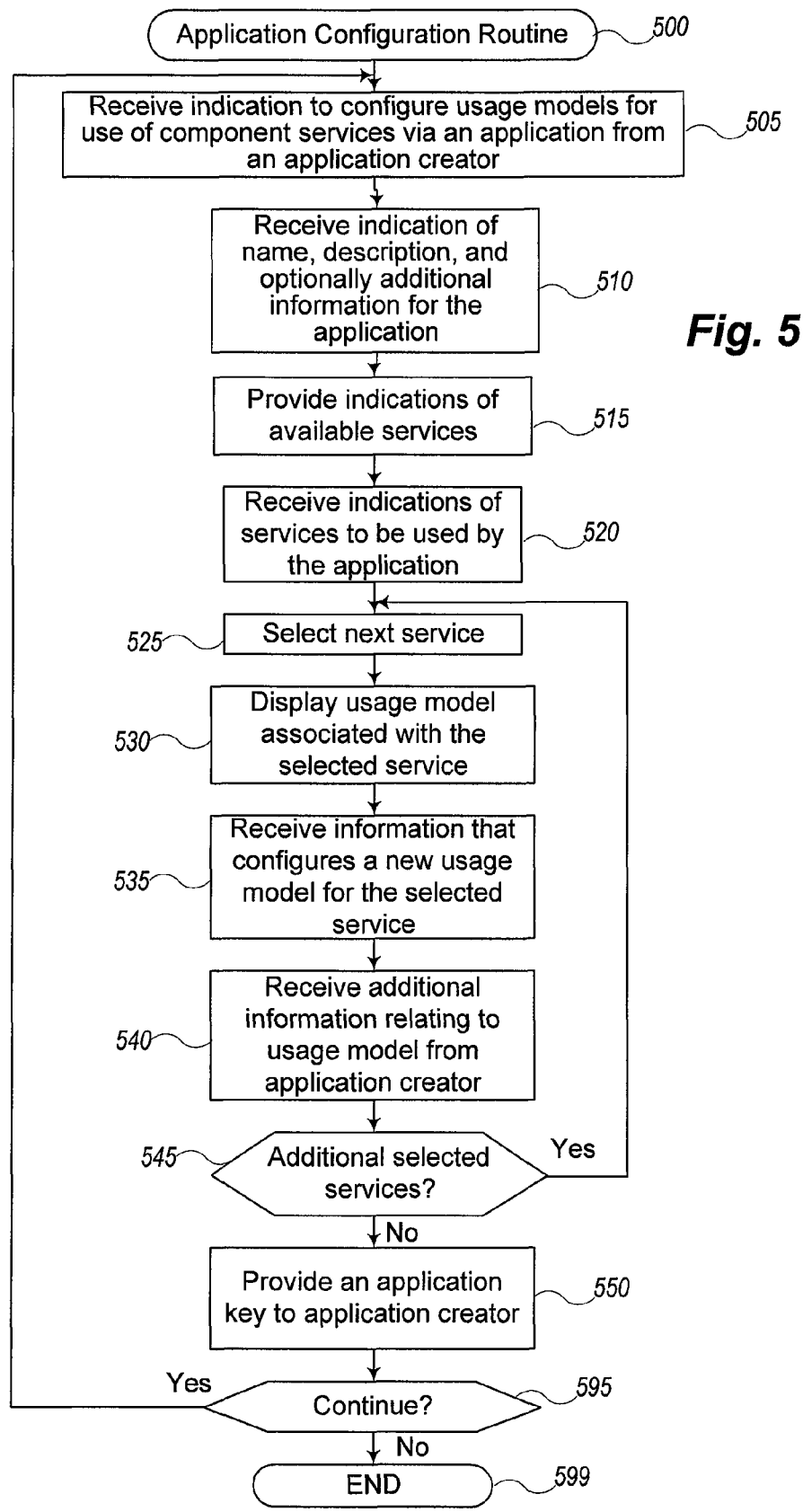
FIG. 5 is a flow diagram of an example embodiment of an Application Configuration routine.

FIG. 5 is a flow diagram of an example embodiment of an Application Configuration routine 500. The routine may, for example, be provided by execution of a configuration component of the CSUF system 110 of FIG. 1A and/or of the CSUF system 440 of FIG. 4, such as to allow application creators to configure usage models for component services used by their applications. In this illustrated example, the usage model configuration is performed in an interactive manner by the application creator, although in other embodiments it may be performed in other manners, such as by the CSUF system automatically determining configured use prices for one or more component services (e.g., by charging a predetermined amount above the default use price or a predetermined multiple of the default use price).

The routine begins at step 505, where the routine receives an indication from an application creator user to configure usage models for one or more component services to be used via an indicated application. In step 510, information is received from the application creator user that indicates a name, a description and optionally additional information for the indicated application. A variety of types of additional information may be specified, and some types of additional information indicated may depend on the type of application. After receiving the information about the application, the routine continues to step 515, where the routine provides indications of one or more available invocable services, such as by displaying them to the application creator user. In some embodiments, some services associated with the CSUF system may not be available for the application (e.g., based on use restrictions in the usage models of various applications, based on previous services selections such as to prevent incompatible scheduled maintenance windows, etc.). In step 520, the routine receives indications of one or more of the invocable services that are selected by the application creator user to be used by the application.

After receiving the indications of the available services, the routine proceeds to step 525, where the next component service is selected, beginning with the first. Once the service is selected, the routine continues to step 530, where the predefined usage model for the service is displayed. After displaying the predefined usage model, the routine continues to step 535, where it receives information from the application creator user for a new configured usage model for use of the selected service via the application. In some embodiments, the CSUF system may assist the application creator user by suggesting various information for the configured usage model, such as one or more suggested configured use prices. After receiving the configured usage model information, the routine proceeds to step 540, where additional information for the usage model may optionally be received from the application creator user and/or the CSUF system for use as part of the configured usage model. A variety of types of additional information may be specified in various embodiments, including timing for obtaining payments (e.g., billing date, billing cycle), promotions, discounts to be provided via discount coupons to be used, etc.

At step 545, the routine determines whether additional invocable services were selected in step 520, and if so the routine returns to step 525. If not, the routine continues to step 550, where in the illustrated embodiment it provides an application key to the application creator user for use with the application. In other embodiments, the application creator user may instead be permitted to specify an application key to be used with the application. In some embodiments, the routine may provide additional information to the application creator user, such as information to direct potential end users of the application to the CSUF system to subscribe to use of the application. After step 550, the routine continues to step 595 to determine whether to continue. If so, the routine returns to step 505, and if not continues to step 599 and ends.

Figure 6:
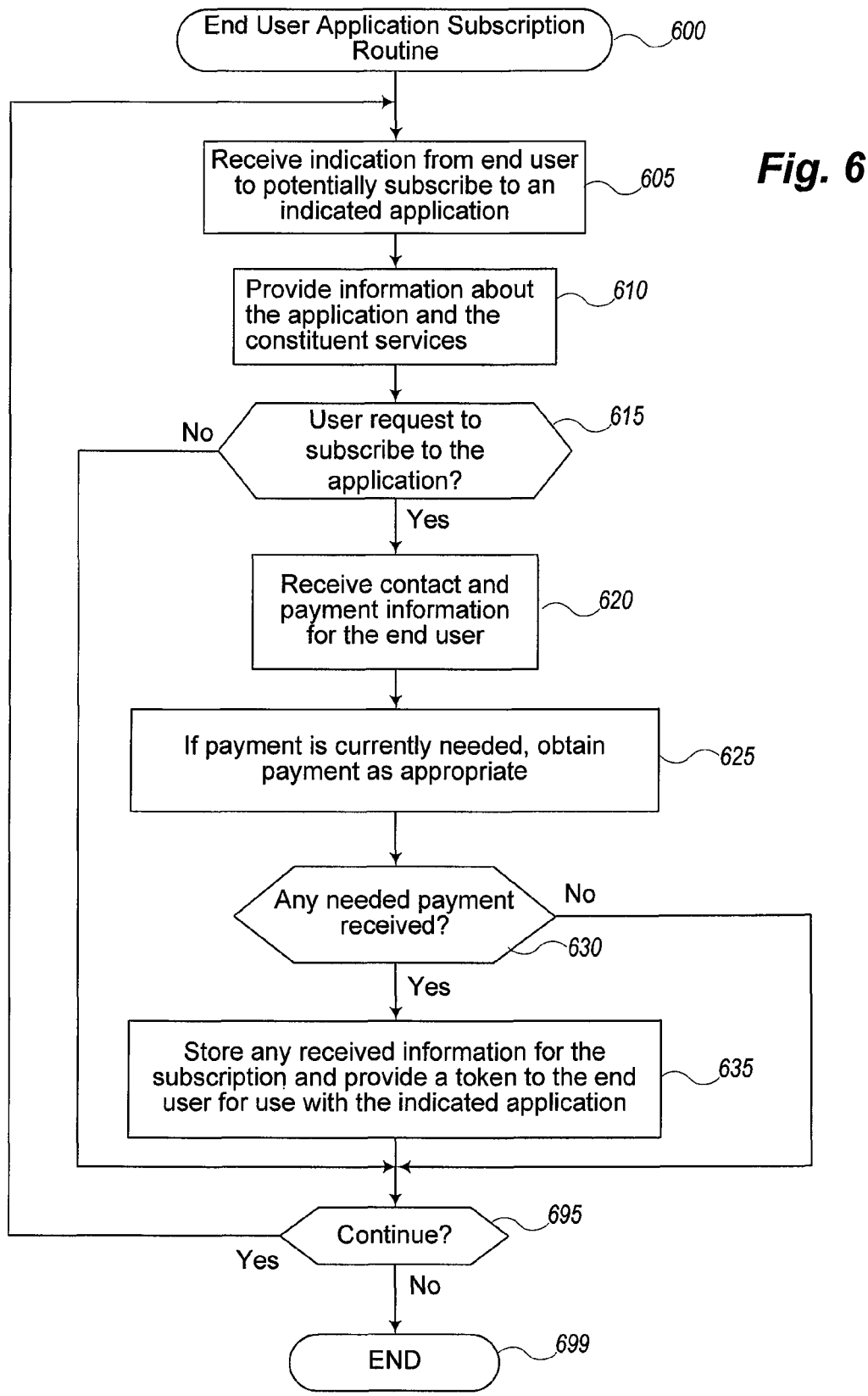
FIG. 6 is a flow diagram of an example embodiment of an End User Application Subscription routine.

FIG. 6 is a flow diagram of an example embodiment of the End User Application Subscription routine 600. The routine may, for example, be provided by execution of a subscription component of the CSUF system 110 of FIG. 1A and/or of the CSUF system 440 of FIG. 4, such as to subscribe end users for use of indicated applications. While in the illustrated embodiment the routine creates subscriptions for end users to enable use of indicated applications, in other embodiments the routine may provide access to indicated applications for end users in other manners.

The routine begins at step 605, where an indication is received from an end user to initiate a potential subscription to an indicated application. The routine then continues to step 610 to display information about the indicated application and the component invocable services to the end user, although in other embodiments some or all of that information may instead not be provided or may be provided in other manners (e.g., already have been displayed to the end user by the application creator, such as on a Web site associated with the application creator). The displayed information may include information about the one or more configured usage models for the indicated application that correspond to the one or more component invocable services used by the application, a description of the application, etc.

After displaying the information to the end user, the routine proceeds to step 615, where the routine determines if the end user has decided to request a subscription to the specified application, such as based on selection by the end user of a corresponding user-selectable control. If so, the routine continues to step 620, and if not proceeds to step 695. At step 620, the routine receives contact and payment information for the end user. In at least some embodiments, the information may be retrieved from an existing account at an associated system if such an account is available. After receiving contact and payment information, the routine proceeds to step 625 to determine whether the subscription to the application has an initial upfront fee (e.g., a one-time setup fee, the first month of a recurring monthly fee, etc.), and if so to attempt to obtain payment for the fee. If it is determined in step 630 that payment is obtained or if no payment is currently needed, the routine proceeds to step 635 to create the subscription and store related information. In addition, in the illustrated embodiment, the routine provides a user token to the end user for use in configuring a copy of the application for use by the end user. In some embodiments, additional functionality (not shown) may be provided, such as to redirect the end user to a Web page from which the end user may download or initiate use of the application. After step 635, the routine continues to step 695. Alternatively, if payment was needed but not received in step 625, then the routine in the illustrated embodiment proceeds from step 630 to step 695 without creating the subscription for the end user. In other embodiments, the routine may instead proceed in other manners, such as to create a subscription for the end user even if the needed payment was not received (or if a determination as to whether the needed payment has been received may not be available until a later time), but to later fail to authenticate access requests if payment is still not received at that time. At step 695, the routine determines whether to continue. If so, the routine returns to step 605, and if not ends at step 699.

While not illustrated here, in some embodiments various additional security mechanisms may be used, such as to ensure that only authorized end users are allowed to subscribe to some or all of the applications. Similarly, in some embodiments various anti-fraud mechanisms may be utilized, such as to ensure that valid payment is received from an end user and/or to prevent abuse of a configured usage model through multiple accounts or violations of use conditions.

Figure 7:
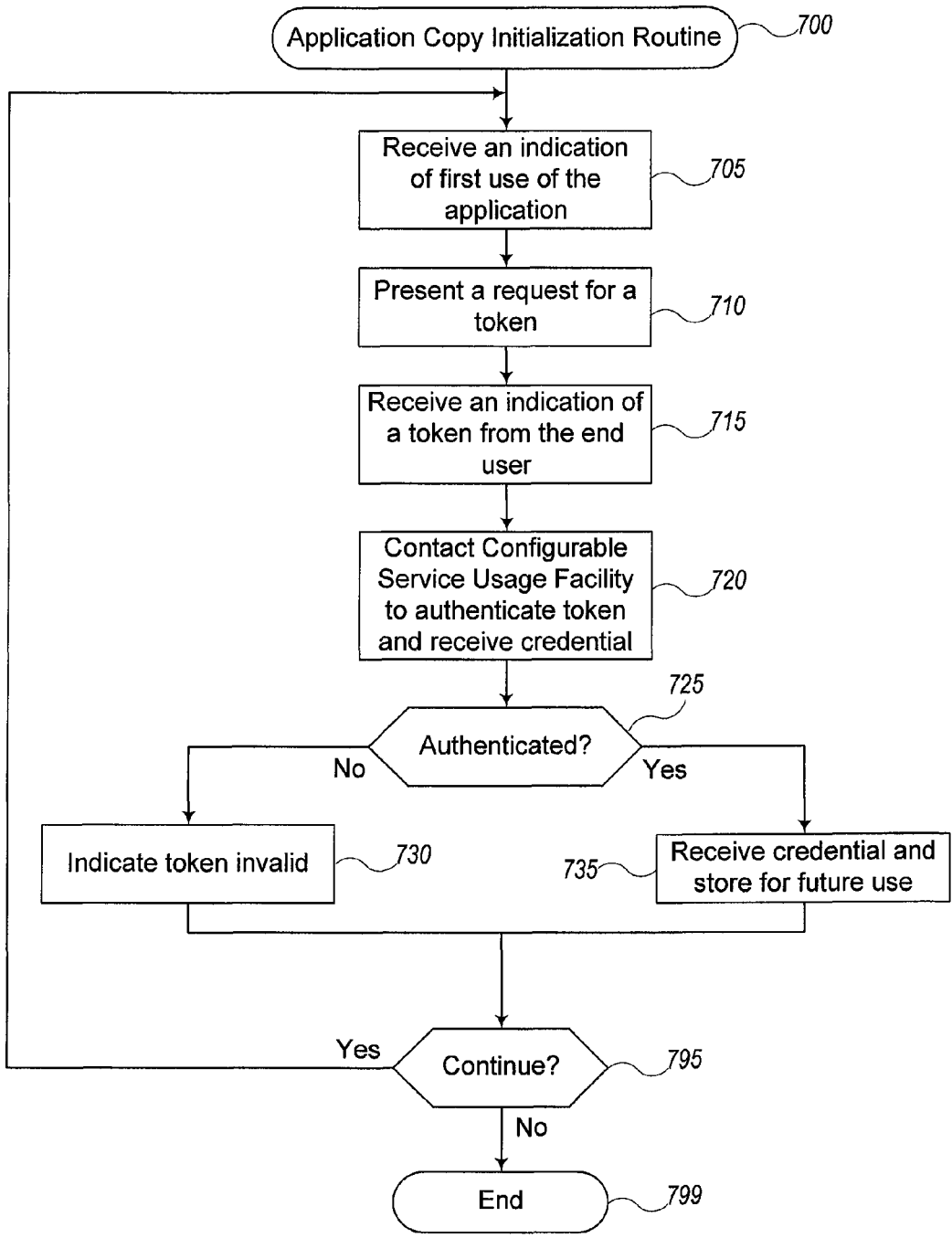
FIG. 7 is a flow diagram of an example embodiment of an Application Copy Initialization routine.

FIG. 7 is a flow diagram of an example embodiment of an Application Copy Initialization routine 700. The routine may, for example, be provided as part of the execution of an application that has one or more configured usage models via the CSUF system, such as application copy 478 of FIG. 4. In the illustrated embodiment, the initialization of an application copy for use by an end user includes configuring the application copy with a user credential for the end user, which will be used when accessing the various component services via the application. However, in other embodiments, a user token may be used instead of a separate user credential. Furthermore, in the illustrated embodiment, the configuration of the application copy with a user credential based on a supplied end user token is performed at the time of initialization of the application copy, but may be performed at other times in other embodiments. For example, in some embodiments the application copy configuration may be delayed until after application copy initialization, such as until the application copy is to invoke a selected invocable service on behalf of an end user. In addition, in some embodiments the application copy may request user tokens and obtain corresponding user credentials multiple times, such as periodically if the user tokens and/or user credentials expire or otherwise become invalid. In such embodiments, an end user may obtain the new user tokens in various ways, such as by interacting with an embodiment of the CSUF system. Furthermore, as previously noted, in at least some embodiments a user credential and/or user token may be revoked or may expire for various reasons, and if so the end user may be prompted to supply a new user token. For example, a user credential and/or user taken may be revoked by the end user (e.g., based on canceling a subscription to an application), or by the application developer and/or the CSUF system (e.g., if the user information may have been compromised, if payment is obtained for use of a service, if a predefined life of the user credential is reached, etc.).

The routine begins at step 705, where an indication of the application initialization process is received (e.g., based on the first use of the application by an end user). The routine then continues to step 710, where it presents a request to the end user for a user token, such as by displaying a user interface to the user. The routine then receives an indication of a user token from the end user in step 715. However, in other types of applications, a user token may be supplied in other manners. After receiving an indication of the user token, the routine proceeds to step 720, where the routine contacts the CSUF system to authenticate the user token. In step 725, the routine determines if the user token was authenticated by the CSUF system. If so, the routine proceeds to step 735 to receive a user credential from the CSUF system that is based on the user token to use when invoking component services on behalf of the end user. If not, the routine proceeds to step 730, where the routine indicates that the user token is invalid, which in some embodiments may prevent the end user from further using the application, or may cause the application to have restricted capabilities (e.g., an inability to use the functionality provided by the component services). After steps 730 or 735, the routine continues to step 795 to determine whether to continue. If so, the routine returns to step 705, and if not continues to step 799 and ends.

Figure 8:
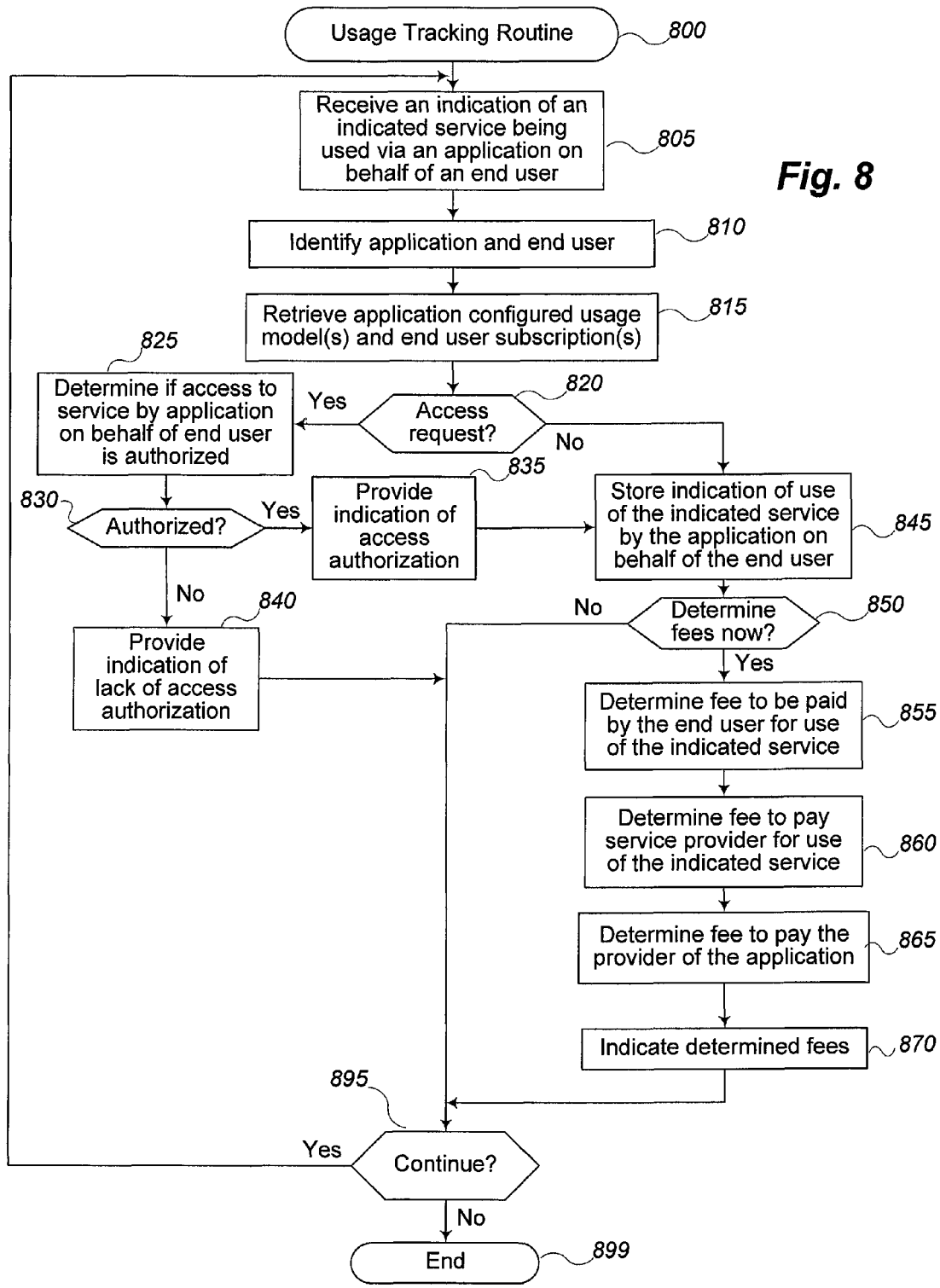
FIG. 8 is a flow diagram of an example embodiment of a Usage Tracking routine.

FIG. 8 is a flow diagram of an example embodiment of a Usage Tracking routine 800. The routine may, for example, be provided by execution of a metering and/or billing component of the CSUF system 110 of FIG. 1A and/or of the CSUF system 440 of FIG. 4, such as to track usage of invocable services by applications on behalf of end users in order to determine fees to be paid by the end users, and to allocate received fees among the application providers and service providers as appropriate.

The routine begins at step 805, where an indication is received that an indicated service is being invoked via a copy of an application on behalf of an end user. The received indication may in some embodiments be received from the indicated service, while in other embodiments made be received from the application copy being used by the end user. Furthermore, in the illustrated embodiment, the received indication may reflect an access request that is performed before the service use occurs, or may reflect an indication of actual service use that is made during or after the service use occurs. The received indication may include an indication of an application key and either a user token or a user credential, and additional information may be received as well (e.g., the amount of use with respect to an indicated use dimension, a starting and/or ending time of use of the service, etc.). After receiving the indication, the routine continues to step 810, where the routine identifies the application performing the invocation of the indicated service and the end user on whose behalf the invocation is performed. In at least some embodiments, the routine identifies the application based on an application key received in step 805, and identifies the end user based on a user credential or token received in step 805. In the illustrated embodiment, the routine then proceeds to step 815 to retrieve information related to the identified application and end user for use in determining access rights to the service and/or for use in determining corresponding fees for the service use, such as any configured usage models for the application and any subscription information for the end user and the application. In other embodiments, however, determinations regarding service use access and/or fee determination may be made in other ways, such as based on information included in a received user credential.

In the illustrated embodiment, the routine next continues to step 820 to determine whether the indication received in step 805 corresponds to an access request to determine whether the application and end user are authorized to use the indicated service. If not, the routine proceeds to step 845 to store information about the use of the indicated service by the application copy on behalf of the end user. If so, the routine instead continues to step 825 to determine if the access is authorized, such as based on the retrieved configured usage models and/or user subscription information, although in other embodiments the determination may be made in other manners (e.g., based on information included in the received user credential). After step 825, the routine continues to step 830 to determine whether the access is authorized, and if not continues to step 840 to provide an indication of a lack of access authorization. If the access is authorized, the routine continues instead to step 835 to provide an indication of access authorization to the indicated service. After step 835, the routine then continues to step 845 to store information about the use of the indicated service by the application copy on behalf of the end user, such as prospectively based on the authorization, although in other embodiments may instead wait to track such use until the routine is notified of the actual use.

After step 845, the routine continues to step 850 to determine whether fees should be determined now, such as if fees are determined for each service use indication, or if a specified amount of time or service use have occurred since a last time that fees were determined. If not, or after step 840, the routine continues to step 895. If fees are to be determined now, however, the routine continues to step 855 to determine one or more fees to be paid by the end user. The fee(s) to be paid by the end user may be determined, for example, by retrieving the configured usage model for use of the indicated service via the application, and applying the configured use price to any currently received information regarding an amount of use of the indicated service. If the fee determination is to be performed for more than just the current service indication, stored information about other service use by one or more application copies of behalf of the end user may be retrieved and similarly used to determine one or more corresponding fees. Once the fee(s) to be paid by the end user are determined, the routine continues to step 860 to determine one or more fees to be paid to the provider of the indicated service and/or to other service providers. A fee to pay a service provider may be determined based on a predefined usage model for the service, as well as any current and/or stored corresponding service usage information. After determining the fees to pay the service provider(s), the routine continues to step 865 to determine the fee(s) to pay the provider(s) of the application(s) whose copies are used on behalf of the end user to invoke the indicated service and/or other services. For example, the fees to pay an application provided may be determined based on the difference between the fees to be paid by the end user for use of the application and the fees to pay the service provider(s) for use of services via the application. In addition, if the CSUF system charges any fees, those fees may be subtracted from the resulting difference. Once the fee(s) to pay the application provider(s) are determined, the routine continues to step 870 to indicate the determined fees. In some embodiments, the indications may be stored until the end user is subsequently charged, while in other embodiments the end user may be charged in response to the indications. Furthermore, while not illustrated here, in some embodiments the routine may further proceed to allocate obtained fees as appropriate between the application provider(s) and the service provider(s), such as by initiating payment to the providers as appropriate.

After step 870, the routine continues to step 895 to determine whether to continue. If so, the routine returns to step 805, and if not continues to step 899 and ends.

Various additional functionality may be provided in various embodiments of the Configurable Service Usage Facility ("CSUF") system. For example, in at least some embodiments, the entity providing the CSUF system and/or third-party service providers may set various criteria to be met by configured usage models for some or all services and/or applications, such as by indicating a minimum configured use price (e.g., a configured use price that exceeds the predefined use price for the service by a predetermined amount) and/or a maximum configured use price. The CSUF system may further enforce any such criteria when configured usage models are created. As a second example, in some embodiments one or more related individuals may be associated with a single user token. For example, if a copy of an application is used by an entity rather than an individual, multiple individuals may be authorized to use a single end user token for a specified application copy. Furthermore, in some embodiments a received application key may be associated with a particular configured usage model for the application, such that, if the application has multiple configured usage models for multiple distinct component services, a distinct application key is issued for each configured usage model.

In addition, in some embodiments configured use prices may have other forms, such as tiered use prices. For instance, tiered use prices may be used to provide volume discounts to high-volume users of an application. When tiered use prices are used, they may be specified in various manners. For example, information may be specified regarding how a tier-based usage model is structured, such as the start and end of various tiers (e.g., in units of the use price for the service, or in terms of conditions such as times for peak/off-peak pricing), whether the tiers are cumulative, etc.

Furthermore, as previously noted, in some embodiments an application creator user may configure a usage model for a component service to use a different use dimension than the use dimensions specified for the predefined usage model for the component service. For example, instead of specifying prices for the use of a storage service based on a number of gigabytes of space used, the configured usage model for an application may specify prices on other bases, such as a price for each DVD stored or for each picture stored. When such custom metering is performed, the application may send information to the CSUF system to indicate when corresponding usage has occurred, such as to indicate that a particular user has stored three pictures. In other situations, the CSUF system may be able to determine at least some such types of corresponding usage automatically without receiving such usage information from an application.

In addition, in some embodiments the CSUF system may enable the use of variable pricing for applications that may be dynamically specified at runtime, such as based on end user negotiation with an application copy being used. If so, when an application creator is interacting with the CSUF system to configure one or more usage models for an application, the application creator may indicate that variable pricing is available to be used with the application. The application creator may then design or configure the application to support such variable pricing. For example, an end user of the application may be able to bid on or otherwise request an indicated price for an amount of use of the application, such as an indicated price that is lower than the price that the application would otherwise charge. The application may then optionally determine to accept or reject the indicated price based on one or more of various factors. For example, the application may accept a lower indicated price based on a minimum volume of use, based on use that occurs at times when demand for use of the application and/or underlying services is low, based on use that is subject to more restrictive terms (e.g., that may be discontinued if specified conditions occur, such as other higher-paying demand occurs), etc. If the application accepts a particular indicated price for use by an end user, the application may then provide information to the CSUF system to specify the price to be charged for corresponding use by the end user, so that the CSUF system may charge the end user the appropriate fees for the use. For example, the application may provide such use price information when the application copy makes a request for a particular use of an invocable service and/or when the application copy provides usage information to the CSUF system.

It will also be appreciated that in some embodiments the functionality provided by the routines discussed above may be provided in alternative ways, such as being split among more routines or consolidated into fewer routines. Similarly, in some embodiments illustrated routines may provide more or less functionality than is described, such as when other illustrated routines instead lack or include such functionality respectively, or when the amount of functionality that is provided is altered. In addition, while various operations may be illustrated as being performed in a particular manner (e.g., in serial or in parallel) and/or in a particular order, those skilled in the art will appreciate that in other embodiments the operations may be performed in other orders and in other manners. Those skilled in the art will also appreciate that the data structures discussed above may be structured in different manners, such as by having a single data structure split into multiple data structures or by having multiple data structures consolidated into a single data structure. Similarly, in some embodiments illustrated data structures may store more or less information than is described, such as when other illustrated data structures instead lack or include such information respectively, or when the amount or types of information that is stored is altered.

From the foregoing it will be appreciated that, although specific embodiments have been described herein for purposes of illustration, various modifications may be made without deviating from the spirit and scope of the invention. Accordingly, the invention is not limited except as by the appended claims and the elements recited therein. In addition, while certain aspects of the invention are presented below in certain claim forms, the inventors contemplate the various aspects of the invention in any available claim form. For example, while only some aspects of the invention may currently be recited as being embodied in a computer-readable medium, other aspects may likewise be so embodied.

What is claimed is:

1. A non-transitory computer-readable medium having stored contents that configure a computing device to track use of invocable services by end users of applications in a configurable manner, by performing a method comprising:

storing, by the configured computing device, information indicating an association of a defined application key with an application and indicating an association of a defined user token with an end user who is using an executing copy of the application;

receiving, by the configured computing device, information indicating a use of an invocable service that has one or more associated pricing terms for use in determining fees for use of the invocable service, wherein the received information includes copies of the defined application key and the defined user token;

determining, by the configured computing device based at least in part on the stored information and on the copies of the defined application key and the defined user token included in the received information, that the use of the invocable service is performed by the executing copy of the application on behalf of the end user;

assessing, by the configured computing device based on the determining that the use of the invocable service is performed by the executing copy of the application on behalf of the end user, multiple fees associated with the use of the invocable service, the assessing including:

obtaining, by the configured computing device, information about a configured usage model for the application that is defined by a provider of the application, wherein the configured usage model specifies one or more configured pricing terms for the application that correspond to use of the invocable service via the application and that are distinct from the one or more associated pricing terms for the invocable service, and wherein the provider of the application is distinct from a provider of the invocable service;

determining, by the configured computing device, a first of the multiple fees that is to be paid by the end user for the use of the invocable service via the application, the first fee being based at least in part on the one or more configured pricing terms for the application;

determining, by the configured computing device, a distinct second of the multiple fees that is to be paid to the provider of the invocable service based on the use of the invocable service via the application, the second fee being based at least in part on the associated pricing terms for the invocable service;

determining, by the configured computing device, a third of the multiple fees that is to be paid to the provider of the application that is based at least in part on a difference between the first and second fees; and providing one or more indications of the first, second and third fees to enable the first fee to be obtained from the end user and to enable the second fee to be provided to the provider of the invocable service and to enable the third fee to be provided to the provider of the application.

2. The non-transitory computer-readable medium of claim 1 wherein the one or more associated pricing terms for the invocable service include an indicated price for an indicated amount of use of the invocable service with respect to an indicated use dimension.

3. The non-transitory computer-readable medium of claim 2 wherein the configured one or more pricing terms for the application include a configured amount of use that differs from the indicated amount of use, or include a configured use dimension that differs from the indicated use dimension for the invocable service.

4. The non-transitory computer-readable medium of claim 1 wherein the method further comprises tracking multiple uses of the invocable service on behalf of the end user by one or more executing copies of one or more applications, and wherein the determining of the first and second fees is performed based on the tracked multiple uses.

5. The non-transitory computer-readable medium of claim 1 wherein the providing of the indications of the first, second and third fees includes obtaining payment from the end user for the first fee.

6. The non-transitory computer-readable medium of claim 1 wherein the method further comprises providing payment of the third fee to the provider of the application in a manner that is based at least in part on obtaining payment for the first fee from the end user.

7. The non-transitory computer-readable medium of claim 1 wherein the providing of the indications of the first, second and third fees includes providing payment of the second fee to the provider of the invocable service in a manner that is based at least in part on obtaining payment for the first fee from the end user.

8. The non-transitory computer-readable medium of claim 1 wherein the determining that the use of the invocable service is performed by the executing copy of the application on behalf of the end user includes identifying the application based at least in part on the copy of the defined application key included in the received information indicating the use of the invocable service.

9. The non-transitory computer-readable medium of claim 8 wherein the stored contents further configure the computing device to, before the receiving of the information indicating the use of the invocable service, receive a copy of the defined application key from the application as part of a request for access to the invocable service, and wherein the method further comprises using the received copy of the defined application key for the request for access to determine that the requested access to the invocable service is authorized and providing an indication that the requested access to the invocable service is determined to be authorized.

10. The non-transitory computer-readable medium of claim 8 wherein the use of the invocable service by the application includes providing, from the executing copy of the application to the invocable service, a copy of the defined application key, and wherein the copy of the defined application key included in the received information indicating the use of the invocable service is provided by the invocable service.

11. The non-transitory computer-readable medium of claim 8 wherein the determining that the use of the invocable service is performed by the executing copy of the application on behalf of the end user includes identifying the end user who is using the executing copy of the application based at least in part on the defined user token included in the received information indicating the use of the invocable service.

12. The non-transitory computer-readable medium of claim 1 wherein the determining of the first fee based at least in part on the configured one or more pricing terms for the application includes determining one or more fees for the end user based on at least one use dimension that is not used by the associated one or more pricing terms for the invocable service.

13. The non-transitory computer-readable medium of claim 1 wherein the invocable service is a Web service accessible by the executing copy of the application over one or more networks.

14. A computer-implemented method comprising:

determining, by one or more configured computing systems, and in response to a request that is from an executing copy of an application for use of an invocable service on behalf of an end user who is using the executing copy, that the use is authorized based at least in part on information specific to the end user;

providing, by the one or more configured computing systems, an indication that the use of the invocable service is authorized;

obtaining, by the one or more configured computing systems, information about a configured usage model for the application that is indicated by a provider of the application, wherein the configured usage model specifies one or more configured pricing terms for the application that correspond to use of the invocable service via the application and that are distinct from one or more pricing terms associated with the invocable service;

determining, by the one or more configured computing systems, a first fee to be paid based on the use of the invocable service via the application, the first fee being based at least in part on the configured one or more pricing terms for the application;

determining, by the one or more configured computing systems, a distinct second fee to be paid to a provider of the invocable service based on the use of the invocable service via the application, the second fee being based at least in part on the associated pricing terms for the invocable service; and providing one or more indications of the first and second fees.

15. The method of claim 14 wherein the providing of the one or more indications of the first and second fees includes initiating obtaining of payment from the end user for the first fee and includes initiating providing of payment of the second fee to the provider of the invocable service.

16. The method of claim 14 further comprising determining a third fee to be paid to the provider of the application, the provider of the application being distinct from the provider of the invocable service and the third fee being based at least in part on a difference between the first and second fees, and initiating providing payment of the third fee to the provider of the application.

17. A configured computing system comprising:
one or more processors; and
one or more modules of a configurable service usage facility that, when executed by at least one of the one or more processors, configure the at least one processor to:
store information indicating an association of a defined application key with an application and indicating an association of a defined user token with a user;
receive information about a request to use an invocable service that has one or more associated pricing terms for use in determining fees for use of the invocable service, wherein the received information includes copies of the defined application key and the defined user token;
determine, based at least in part on the stored information and on the included copies of the defined application key and the defined user token in the received information, that the requested use of the invocable service occurs via an executing copy of the application on behalf of the user who is using the executing copy of the application, and that the requested use of the invocable service is authorized based at least in part on information specific to the user;
provide an indication that the requested use of the invocable service is authorized;
determine a first fee to be paid based on use of the invocable service via the application, the first fee being based at least in part on configured one or more configured pricing terms for the application for use in determining fees to be paid for use of the invocable service via the application;
determine a second fee to be paid to a provider of the invocable service based on use of the invocable service via the application, the second fee being based at least in part on the associated pricing terms for the invocable service;
determine a third fee to be paid to a provider of the application based at least in part on the first and second fees; and
provide one or more indications of the first, second and third fees.

18. The computing system of claim 17 wherein the providing of the one or more indications of the first, second and third fees includes initiating obtaining of payment from the user for the first fee and includes initiating providing of payment of the second fee to the provider of the invocable service.

19. The computing system of claim 18 wherein the first and second fees are distinct, wherein the providers of application and the invocable service are distinct, and wherein the third fee is based at least in part on a difference between the first and second fees.

20. The computing system of claim 17 wherein the one or more modules includes software instructions for execution by the one or more processors of the computing system.

21. The computing system of claim 17 wherein the one or more modules further configure the at least one processor to obtain information about a configured usage model for the application that is specified by the provider of the application, and wherein the configured usage model specifies the one or more configured pricing terms for use in determining the fees to be paid for the use of the invocable service via the application.

22. The computing system of claim 21 wherein the one or more modules further configure the at least one processor to obtain information about an associated usage model for the invocable service that is specified by the provider of the invocable service, wherein the associated usage model specifies the one or more associated pricing terms for use in determining the fees for the use of the invocable service, and wherein the providers of application and the invocable service are distinct.

23. The computing system of claim 17 wherein the one or more configured pricing terms include a configured amount of use of the invocable service that differs from an amount of use of the invocable service indicated by the one or more associated pricing terms, or include a configured use dimension for the invocable service that differs from a use dimension indicated for the invocable service by the one or more associated pricing terms.

24. The computing system of claim 17 wherein the information specific to the user includes a subscription of the user for the invocable service.

25. The method of claim 14 further comprising, before the request for use of the invocable service, storing information indicating an association of a defined application key with the application and indicating an association of a defined user token with the end user,
and wherein the request for the use of the invocable service includes copies of the defined application key and of the defined user token; and
wherein the determining that the use of the invocable service is authorized includes determining that the requested use is on behalf of the application and the end user based at least in part on the stored information and on the copies of the defined application key and of the defined user token included in the request.

26. The method of claim 14 further comprising:
before the use of the invocable service, storing information indicating an association of a defined application key with the application and indicating an association of a defined user token with the end user;
after the use of the invocable service, receiving information indicating that the use of the invocable service has occurred, the received information including copies of the defined application key and of the defined user token; and
determining that the use occurred on behalf of the application and the end user based at least in part on the stored information and on the copies of the defined application key and of the defined user token included in the received information indicating that the use of the invocable service has occurred.

27. The method of claim 14 wherein the information specific to the end user includes a subscription of the end user for the invocable service.

28. The non-transitory computer-readable medium of claim 1 wherein the stored contents include instructions that, when executed, further configure the computing device to:
before the use of the invocable service by the executing copy of the application on behalf of the end user, receive a request that is to perform the use of the invocable service and that includes copies of the defined application key and the defined user token;
determine, based at least in part on the stored information and on the copies of the defined application key and the defined user token included with the received request, that the requested use of the invocable service is authorized; and
provide an indication that the requested use of the invocable service is determined to be authorized.

29. The non-transitory computer-readable medium of claim 28 wherein the determining that the use of the invocable service is authorized is further based at least in part on a subscription of the end user for the invocable service.

30. The non-transitory computer-readable medium of claim 28 wherein the determining that the use of the invocable service is authorized is further based at least in part on a subscription of the end user for the application.

* * * * *